United States Patent
Bara et al.

(10) Patent No.: US 12,129,320 B2
(45) Date of Patent: Oct. 29, 2024

(54) MATERIALS FOR REDUCING ACIDS FROM LIQUID PHASES

(71) Applicant: The Board of Trustees of the University of Alabama, Tuscaloosa, AL (US)

(72) Inventors: Jason Edward Bara, Tuscaloosa, AL (US); Steven Thomas Weinman, Northport, AL (US)

(73) Assignee: The Board of Trustees of the University of Alabama, Tuscaloosa, AL (US)

( * ) Notice: Subject to any disclaimer, the term of this patent is extended or adjusted under 35 U.S.C. 154(b) by 28 days.

(21) Appl. No.: 17/410,480

(22) Filed: Aug. 24, 2021

(65) Prior Publication Data
US 2022/0056181 A1 Feb. 24, 2022

Related U.S. Application Data

(60) Provisional application No. 63/069,366, filed on Aug. 24, 2020.

(51) Int. Cl.
| | |
|---|---|
| C08F 26/06 | (2006.01) |
| B01D 71/28 | (2006.01) |
| B01D 71/44 | (2006.01) |
| B01D 71/72 | (2006.01) |
| C07D 233/64 | (2006.01) |
| C07D 235/10 | (2006.01) |
| C08F 212/08 | (2006.01) |
| C08F 226/06 | (2006.01) |
| B01D 71/74 | (2006.01) |

(52) U.S. Cl.
CPC ............ *C08F 226/06* (2013.01); *B01D 71/28* (2013.01); *B01D 71/72* (2013.01); *C07D 233/64* (2013.01); *C07D 235/10* (2013.01); *C08F 212/08* (2013.01); *B01D 71/74* (2013.01); *C08F 26/06* (2013.01)

(58) Field of Classification Search
None
See application file for complete search history.

(56) References Cited

U.S. PATENT DOCUMENTS

| | | | |
|---|---|---|---|
| 5,218,009 A | 6/1993 | Rutsch et al. | |
| 5,472,992 A | 12/1995 | Leppard et al. | |

(Continued)

FOREIGN PATENT DOCUMENTS

| | | | |
|---|---|---|---|
| WO | WO-2005047281 A1 * | 5/2005 | ............ A01N 43/54 |
| WO | 2013173547 | 11/2013 | |
| WO | 2014007163 | 1/2014 | |

OTHER PUBLICATIONS

Alkahtani, H. M. et al., "Synthesis and biological evaluation of benzo[d]imidazole derivatives as potential anti-cancer agents". Bioorganic & Medicinal Chemistry Letters 2012, 22(3), 1317-1321. (Year: 2012).*

(Continued)

*Primary Examiner* — Richard A Huhn
(74) *Attorney, Agent, or Firm* — Meunier Carlin & Curfman LLC

(57) ABSTRACT

Imidazole-containing polymer membranes and resins are described herein. Methods of their preparation and use are also described herein. The methods of using the membranes and resins include reducing acids from liquid phases.

8 Claims, 1 Drawing Sheet vinyl-type or styrene-type heat or UV

N = acid-binding sites

(56) References Cited

U.S. PATENT DOCUMENTS

| | | |
|---|---|---|
| 6,489,376 B1 | 12/2002 | Khudyakov et al. |
| 7,521,015 B2 | 4/2009 | Cheng et al. |
| 7,767,728 B2 | 8/2010 | Lu et al. |
| 2017/0297926 A1 | 10/2017 | Nickelsen et al. |

OTHER PUBLICATIONS

Abedini, A.; Crabtree, E.; Bara, J. E.; Turner, C. H., Molecular analysis of selective gas adsorption within composites of ionic polyimides and ionic liquids as gas separation membranes. Chemical Physics 2019, 516, 71-83.

Abedini, A.; Crabtree, E.; Bara, J. E.; Turner, C. H., Molecular Simulation of Ionic Polyimides and Composites with Ionic Liquids as Gas-Separation Membranes. Langmuir 2017, 33, 11377-11389.

Ahmed, M. B.; Alam, M. M.; Zhou, J. L.; Xu, B.; Johir, M. A. H.; Karmakar, A. K.; Rahman, M. S.; Hossen, J.; Hasan, A. T. M. K.; Moni, M. A., Advanced treatment technologies efficacies and mechanism of per- and poly-fluoroalkyl substances removal from water. Process Safety and Environmental Protection 2020, 136, 1-14.

AlMarzooqi, F. A.; Bilad, M. R.; Mansoor, B.; Arafat, H. A., A comparative study of image analysis and porometry techniques for characterization of porous membranes. Journal of Materials Science 2016, 51 (4), 2017-2032.

Almeida, K. M. d.; Almeida, M. M.; Fingola, F. F.; Ferraz, H. C., Membrane adsorber for endotoxin removal. Brazilian Journal of Pharmaceutical Sciences 2016, 52, 171-178.

Anderson, E.B. and Long, T.E., 2010. Imidazole- and imidazolium-containing polymers for biology and material science applications. Polymer, 51(12), pp. 2447-2454.

Arhangelskis, M.; Katsenis, A. D.; Novendra, N.; Akimbekov, Z.; Gandrath, D.; Marrett, J. M.; Ayoub, G.; Morris, A. J.; Farha, O. K.; Friščić, T.; Navrotsky, A., Theoretical Prediction and Experimental Evaluation of Topological Landscape and Thermodynamic Stability of a Fluorinated Zeolitic Imidazolate Framework. Chemistry of Materials 2019, 31 (10), 3777-3783.

Ateia, M.; Maroli, A.; Tharayil, N.; Karanfil, T., The overlooked short- and ultrashort-chain poly- and perfluorinated substances: A review. Chemosphere 2019, 220, 866-882.

Ateia, Mohamed, et al. "Cationic polymer for selective removal of GenX and short-chain PFAS from surface waters and wastewaters at ng/L levels." Water research 163 (2019): 114874.

Ateia, Mohamed, et al. "Efficient PFAS removal by amine-functionalized sorbents: critical review of the current literature." Environmental Science & Technology Letters 6.12 (2019): 688-695.

Banks, D.; Jun, B.-M.; Heo, J.; Her, N.; Park, C. M.; Yoon, Y., Selected advanced water treatment technologies for perfluoroalkyl and polyfluoroalkyl substances: A review. Separation and Purification Technology 2020, 231, 115929.

Bara, J.E., Camper, D.E., Gin, D.L. and Noble, R.D., 2010. Room-temperature ionic liquids and composite materials: platform technologies for CO2 capture. Accounts of Chemical Research, 43(1), pp. 152-159.

Bara JE, Lessmann S, Gabriel CJ, Hatakeyama ES, Noble RD, Gin DL. Synthesis and performance of polymerizable room-temperature ionic liquids as gas separation membranes. Industrial & engineering chemistry research. Aug. 1, 2007;46(16):5397-404.

Bara JE, Gin DL, Noble RD. Effect of anion on gas separation performance of polymer-room-temperature ionic liquid composite membranes. Industrial & engineering chemistry research. Dec. 17, 2008;47(24):9919-24.

Bara JE, Noble RD, Gin DL. Effect of "Free" cation substituent on gas separation performance of polymer-room-temperature ionic liquid composite membranes. Industrial & engineering chemistry research. May 6, 2009;48(9):4607-10.

Bara JE, Kaminski AK, Noble RD, Gin DL. Influence of nanostructure on light gas separations in cross-linked lyotropic liquid crystal membranes. Journal of membrane science. Feb. 1, 2007;288(1-2):13-9.

Bara JE, Hatakeyama ES, Gabriel CJ, Zeng X, Lessmann S, Gin DL, Noble RD. Synthesis and light gas separations in cross-linked gemini room temperature ionic liquid polymer membranes. Journal of Membrane Science. May 15, 2008;316(1-2):186-91.

Bara JE, Gabriel CJ, Hatakeyama ES, Carlisle TK, Lessmann S, Noble RD, Gin DL. Improving CO2 selectivity in polymerized room-temperature ionic liquid gas separation membranes through incorporation of polar substituents. Journal of Membrane Science. Aug. 1, 2008;321(1):3-7.

Bara JE, Hatakeyama ES, Gin DL, Noble RD. Improving CO2 permeability in polymerized room-temperature ionic liquid gas separation membranes through the formation of a solid composite with a room-temperature ionic liquid. Polymers for Advanced Technologies. Oct. 2008;19(10):1415-20.

Bara, J. E.; Moon, J. D.; Reclusado, K. R.; Whitley, J. W., COSMOTherm as a Tool for Estimating the Thermophysical Properties of Alkylimidazoles as Solvents for CO2 Separations. Industrial & Engineering Chemistry Research 2013, 52 (15), 5498-5506.

Bara, J. E.; O'Harra, K. E.; Durbin, M. M.; Dennis, G. P.; Jackson, E. M.; Thomas, B.; Odutola, J. A., Synthesis and Characterization of Ionene-Polyamide Materials as Candidates for New Gas Separation Membranes. MRS Advances 2018, 3, 3091-3102.

Boi, C.; Malavasi, A.; Carbonell, R. G.; Gilleskie, G., A direct comparison between membrane adsorber and packed column chromatography performance. Journal of Chromatography A 2020, 1612, 460629.

Boo, C.; Wang, Y.; Zucker, I.; Choo, Y.; Osuji, C. O.; Elimelech, M., High Performance Nanofiltration Membrane for Effective Removal of Perfluoroalkyl Substances at High Water Recovery. Environmental Science & Technology 2018, 52 (13), 7279-7288.

Brämer, C.; Tünnermann, L.; Gonzalez Salcedo, A.; Reif, O.-W.; Solle, D.; Scheper, T.; Beutel, S., Membrane Adsorber for the Fast Purification of a Monoclonal Antibody Using Protein A Chromatography. Membranes 2019, 9 (12), 159.

Busch, J.; Ahrens, L.; Sturm, R.; Ebinghaus, R., Polyfluoroalkyl compounds in landfill leachates. Environmental Pollution 2010, 158 (5), 1467-1471.

Cao, X.; Luo, J.; Woodley, J. M.; Wan, Y., Bioinspired Multifunctional Membrane for Aquatic Micropollutants Removal. ACS Applied Materials & Interfaces 2016, 8 (44), 30511-30522.

Chen, W.; Zhang, X.; Zhang, Y.; Mamadiev, M., Facile and efficient synthesis of polyacrylonitrile-based functional fibers and its sorption properties of perfluorooctane sulfonate and perfluorooctanoate. Journal of Molecular Liquids 2017, 241, 1013-1022.

Chenette, H. C.; Robinson, J. R.; Hobley, E.; Husson, S. M., Development of high-productivity, strong cation-exchange adsorbers for protein capture by graft polymerization from membranes with different pore sizes. Journal of Membrane Science 2012, 423, 43-52.

Chenette, H. C.; Welsh, J. M.; Husson, S. M., Affinity membrane adsorbers for binding arginine-rich proteins. Separation Science and Technology 2017, 52 (2), 276-286.

Chi, H.-Y.; Hung, S.-H.; Kan, M.-Y.; Lee, L.-W.; Lam, C. H.; Chen, J.-J.; Kang, D.-Y., Metal-organic frameworks for dye sorption: structure-property relationships and scalable deposition of the membrane adsorber. CrystEngComm 2018, 20 (36), 5465-5474.

Chitpong, N.; Husson, S. M., High-capacity, nanofiber-based ion-exchange membranes for the selective recovery of heavy metals from impaired waters. Separation and Purification Technology 2017, 179, 94-103.

Chitpong, N.; Husson, S. M., Polyacid functionalized cellulose nanofiber membranes for removal of heavy metals from impaired waters. Journal of Membrane Science 2017, 523, 418-429.

Chitpong, N.; Husson, S., Nanofiber Ion-Exchange Membranes for the Rapid Uptake and Recovery of Heavy Metals from Water. Membranes 2016, 6 (4), 59.

Chu, S.; Letcher, R. J.; McGoldrick, D. J.; Backus, S. M., A New Fluorinated Surfactant Contaminant in Biota: Perfluorobutane Sulfonamide in Several Fish Species. Environmental Science & Technology 2016, 50 (2), 669-675.

Cole, W. T. S.; Wei, H.; Nguyen, S. C.; Harris, C. B.; Miller, D. J.; Saykally, R. J., Dynamics of Micropollutant Adsorption to Poly-

(56) References Cited

OTHER PUBLICATIONS styrene Surfaces Probed by Angle-Resolved Second Harmonic Scattering. The Journal of Physical Chemistry C 2019, 123 (23), 14362-14369.

Crone, B. C.; Speth, T. F.; Wahman, D. G.; Smith, S. J.; Abulikemu, G.; Kleiner, E. J.; Pressman, J. G., Occurrence of per- and polyfluoroalkyl substances (PFAS) in source water and their treatment in drinking water. Critical Reviews in Environmental Science and Technology 2019, 49 (24), 2359-2396.

Cui, J.; Gao, P.; Deng, Y., Destruction of Per- and Polyfluoroalkyl Substances (PFAS) with Advanced Reduction Processes (ARPs): A Critical Review. Environmental Science & Technology 2020, 54 (7), 3752-3766.

De Vries, I.; Schreiber, S.; Boßmann, D.; Hellmann, Z.; Kopatz, J.; Neumann, H.; Beutel, S., Single-use membrane adsorbers for endotoxin removal and purification of endogenous polysialic acid from *Escherichia coli* K1. Biotechnology Reports 2018, 17, 110-116.

Demarteau, J.; O'Harra, K. E.; Bara, J. E.; Sardon, H., Valorization of Plastic Wastes for the Synthesis of Imidazolium-Based Self-Supported Elastomeric Ionenes. ChemSusChem 2020, 13 (12), 3122-3126.

Deng, S.; Yu, Q.; Huang, J.; Yu, G., Removal of perfluorooctane sulfonate from wastewater by anion exchange resins: Effects of resin properties and solution chemistry. Water Research 2010, 44 (18), 5188-5195.

Dombrowski, P. M.; Kakarla, P.; Caldicott, W.; Chin, Y.; Sadeghi, V.; Bogdan, D.; Barajas-Rodriguez, F.; Chiang, S.-Y., Technology review and evaluation of different chemical oxidation conditions on treatability of PFAS. Remediation Journal 2018, 28 (2), 135-150.

Du, Z.; Deng, S.; Bei, Y.; Huang, Q.; Wang, B.; Huang, J.; Yu, G., Adsorption behavior and mechanism of perfluorinated compounds on various adsorbents—A review. Journal of Hazardous Materials 2014, 274, 443-454.

Du, Z.; Deng, S.; Chen, Y.; Wang, B.; Huang, J.; Wang, Y.; Yu, G., Removal of perfluorinated carboxylates from washing wastewater of perfluorooctanesulfonyl fluoride using activated carbons and resins. Journal of Hazardous Materials 2015, 286, 136-143.

Duval, C. E.; Darge, A. W.; Ruff, C.; DeVol, T. A.; Husson, S. M., Rapid Sample Preparation for Alpha Spectroscopy with Ultrafiltration Membranes. Analytical Chemistry 2018, 90 (6), 4144-4149.

Emel'yanenko VN, Portnova SV, Verevkin SP, Skrzypczak A, Schubert T. Building blocks for ionic liquids: Vapor pressures and vaporization enthalpies of 1-(n-alkyl)-imidazoles. The Journal of Chemical Thermodynamics. Oct. 1, 2011;43(10):1500-5.

Fan, J.; Luo, J.; Wan, Y., Aquatic micro-pollutants removal with a biocatalytic membrane prepared by metal chelating affinity membrane chromatography. Chemical Engineering Journal 2017, 327, 1011-1020.

Fan, J.; Luo, J.; Wan, Y., Membrane chromatography for fast enzyme purification, immobilization and catalysis: A renewable biocatalytic membrane. Journal of Membrane Science 2017, 538, 68-76.

Flowers, B. S.; Mittenthal, M. S.; Jenkins, A. H.; Wallace, D. A.; Whitley, J. W.; Dennis, G. P.; Wang, M.; Turner, C. H.; Emel'yanenko, V. N.; Verevkin, S. P.; Bara, J. E., 1,2,3-Trimethoxypropane: A Glycerol-Derived Physical Solvent for CO2 Absorption. ACS Sustainable Chem. Eng. 2017, 5 (1), 911-921.

Gagliano, Erica, et al. "Removal of poly- and perfluoroalkyl substances (PFAS) from water by adsorption: Role of PFAS chain length, effect of organic matter and challenges in adsorbent regeneration." Water research 171 (2020): 115381.

Gao, Y.; Deng, S.; Du, Z.; Liu, K.; Yu, G., Adsorptive removal of emerging polyfluoroalky substances F-53B and PFOS by anion-exchange resin: A comparative study. Journal of Hazardous Materials 2017, 323, 550-557.

Garist, I. V.; Verevkin, S. P.; Bara, J. E.; Hindman, M. S.; Danielsen, S. P. O., Building Blocks for Ionic Liquids: Vapor Pressures and Vaporization Enthalpies of 1-(n-Alkyl)-benzimidazoles. Journal of Chemical & Engineering Data 2012, 57 (6), 1803-1809.

Garist, I. V.; Verevkin, S. P.; Samarov, A. A.; Bara, J. E.; Hindman, M. S.; Danielsen, S. P. O., Building Blocks for Ionic Liquids: Vapor Pressures and Vaporization Enthalpies of Alkoxy Derivatives of Imidazole and Benzimidazole. Industrial & Engineering Chemistry Research 2012, 51 (47), 15517-15524.

Goss, K.-U., The pKa Values of PFOA and Other Highly Fluorinated Carboxylic Acids. Environmental Science & Technology 2008, 42 (2), 456-458.

Green MD, Allen Jr MH, Dennis JM, Salas-de la Cruz D, Gao R, Winey KI, Long TE. Tailoring macromolecular architecture with imidazole functionality: A perspective for controlled polymerization processes. European polymer journal. Apr. 1, 2011;47(4):486-96.

Hamilton, J. R.; Abedini, A.; Zhang, Z.; Whitley, J. W.; Bara, J. E.; Turner, C. H., Enhancing the pre-polymerization coordination of 1-vinylimidazole. Chemical Engineering Science 2015, 138, 646-654.

Han, B.; Carvalho, W.; Canilha, L.; da Silva, S. S.; Almeida e Silva, J. B.; McMillan, J. D.; Wickramasinghe, S. R., Adsorptive membranes vs. resins for acetic acid removal from biomass hydrolysates. Desalination 2006, 193 (1), 361-366.

Hogue, C., 3M admits to unlawful release of PFAS in Alabama. Chemical & Engineering News Jun. 25, 2019.

Hu, X. C.; et al., Detection of poly- and perfluoroalkyl substances (PFASs) in US drinking water linked to industrial sites, military fire training areas, and wastewater treatment plants. Environmental Science & Technology Letters 2016, 3 (10), 344-350.

Ji, B.; Kang, P.; Wei, T.; Zhao, Y., Challenges of aqueous per- and polyfluoroalkyl substances (PFASs) and their foreseeable removal strategies. Chemosphere 2020, 250, 126316.

Kammakakam, I.; O'Harra, K. E.; Dennis, G. P.; Jackson, E. M.; Bara, J. E., Self-healing imidazolium-based ionene-polyamide membranes: an experimental study on physical and gas transport properties. Polymer International 2019, 68 (6), 1123-1129.

Khulbe, K. C.; Matsuura, T., Removal of heavy metals and pollutants by membrane adsorption techniques. Applied Water Science 2018, 8 (1), 19.

Kucharzyk, K. H.; Darlington, R.; Benotti, M.; Deeb, R.; Hawley, E., Novel treatment technologies for PFAS compounds: A critical review. Journal of Environmental Management 2017, 204, 757-764.

Kwiatkowski, C. F.; Andrews, D. Q.; Birnbaum, L. S.; Bruton, T. A.; DeWitt, J. C.; Knappe, D. R. U.; Maffini, M. V.; Miller, M. F.; Pelch, K. E.; Reade, A.; Soehl, A.; Trier, X.; Venier, M.; Wagner, C. C.; Wang, Z.; Blum, A., Scientific Basis for Managing PFAS as a Chemical Class. Environmental Science & Technology Letters 2020.

Labanda, J.; Sabaté, J.; Llorens, J., Experimental and modeling study of the adsorption of single and binary dye solutions with an ion-exchange membrane adsorber. Chemical Engineering Journal 2011, 166 (2), 536-543.

Labanda, J.; Sabaté, J.; Llorens, J., Modeling of the dynamic adsorption of an anionic dye through ion-exchange membrane adsorber. Journal of Membrane Science 2009, 340(1), 234-240.

Lee, L.-W.; Pao, S.-Y.; Pathak, A.; Kang, D.-Y.; Lu, K.-L., Membrane adsorber containing a new Sm (III)-organic framework for dye removal. Environmental Science: Nano 2019, 6 (4), 1067-1076.

Lenarcik, B.; Ojczenasz, P., The influence of the size and position of the alkyl groups in alkylimidazole molecules on their acid-base properties. Journal of Heterocyclic Chemistry 2002, 39 (2), 287-290.

Lindstrom, A. B.; Strynar, M. J.; Delinsky, A. D.; Nakayama, S. F.; McMillan, L.; Libelo, E. L.; Neill, M.; Thomas, L., Application of WWTP biosolids and resulting perfluorinated compound contamination of surface and well water in Decatur, Alabama, USA. Environmental Science & Technology 2011, 45 (19), 8015-8021.

Liu, H.; Bara, J. E.; Turner, C. H., DFT study on the effect of exocyclic substituents on the proton affinity of 1-methylimidazole. Chemical Physics 2013, 416, 21-25.

Liu, H.; Bara, J. E.; Turner, C. H., Tuning the Adsorption Interactions of Imidazole Derivatives with Specific Metal Cations. The Journal of Physical Chemistry A 2014, 118 (22), 3944-3951.

(56) References Cited

OTHER PUBLICATIONS

Liu, H.; Zhang, Z.; Bara, J. E.; Turner, C. H., Electrostatic Potential within the Free Volume Space of Imidazole-Based Solvents: Insights into Gas Absorption Selectivity. The Journal of Physical Chemistry B 2014, 118 (1), 255-264.

Liu, J.; Mejia Avendaño, S., Microbial degradation of polyfluoroalkyl chemicals in the environment: A review. Environment International 2013, 61, 98-114.

Liu, L.; Luo, J.; Wan, Y.; Chen, X.; Wu, Y., Mussel-Inspired Membrane Adsorber with Thiol Ligand for Patulin Removal: Adsorption and Regeneration Behaviors. Macromolecular Materials and Engineering 2019, 304 (6), 1800790.

Liu, Z.; Wickramasinghe, S. R.; Qian, X., Membrane chromatography for protein purifications from ligand design to functionalization. Separation Science and Technology 2017, 52 (2), 299-319.

Lu, D.; Sha, S.; Luo, J.; Huang, Z.; Zhang Jackie, X., Treatment train approaches for the remediation of per- and polyfluoroalkyl substances (PFAS): A critical review. Journal of Hazardous Materials 2020, 386, 121963.

Ma, N.; Yao, D.; Yang, H.; Yin, J.; Wang, H.; Zhang, Y.; Meng, J., Surface Modification of Cellulose Membranes to Prepare a High-Capacity Membrane Adsorber for Monoclonal Antibody Purification via Hydrophobic Charge-Induction Chromatography. Industrial & Engineering Chemistry Research 2018, 57 (39), 13235-13246.

Maimaiti, A.; Deng, S.; Meng, P.; Wang, W.; Wang, B.; Huang, J.; Wang, Y.; Yu, G., Competitive adsorption of perfluoroalkyl substances on anion exchange resins in simulated AFFF-impacted groundwater. Chemical Engineering Journal 2018, 348, 494-502.

McCaffrey, D. L.; Nguyen, S. C.; Cox, S. J.; Weller, H.; Alivisatos, A. P.; Geissler, P. L.; Saykally, R. J., Mechanism of ion adsorption to aqueous interfaces: Graphene/water vs. air/water. Proceedings of the National Academy of Sciences 2017, 114 (51), 13369.

Merino, N.; Qu, Y.; Deeb, R. A.; Hawley, E. L.; Hoffmann, M. R.; Mahendra, S., Degradation and Removal Methods for Perfluoroalkyl and Polyfluoroalkyl Substances in Water. Environmental Engineering Science 2016, 33 (9), 615-649.

Mullins, E.; Oldland, R.; Liu, Y. A.; Wang, S.; Sandler, S. I.; Chen, C.-C.; Zwolak, M.; Seavey, K. C., Sigma-Profile Database for Using COSMO-Based Thermodynamic Methods. Industrial & Engineering Chemistry Research 2006, 45 (12), 4389-4415.

Newton, S.; McMahen, R.; Stoeckel, J. A.; Chislock, M.; Lindstrom, A.; Strynar, M., Novel Polyfluorinated Compounds Identified Using High Resolution Mass Spectrometry Downstream of Manufacturing Facilities near Decatur, Alabama. Environmental Science & Technology 2017, 51 (3), 1544-1552.

Nzeribe, B. N.; Crimi, M.; Mededovic Thagard, S.; Holsen, T. M., Physico-Chemical Processes for the Treatment of Per- and Polyfluoroalkyl Substances (PFAS): A review. Critical Reviews in Environmental Science and Technology 2019, 49 (10), 866-915.

Otten, D. E.; Shaffer, P. R.; Geissler, P. L.; Saykally, R. J., Elucidating the mechanism of selective ion adsorption to the liquid water surface. Proceedings of the National Academy of Sciences 2012, 109 (3), 701.

Phong Vo, H. N.; Ngo, H. H.; Guo, W.; Hong Nguyen, T. M.; Li, J.; Liang, H.; Deng, L.; Chen, Z.; Hang Nguyen, T. A., Poly- and perfluoroalkyl substances in water and wastewater: A comprehensive review from sources to remediation. Journal of Water Process Engineering 2020, 36, 101393.

Remucal, C. K., Spatial and temporal variability of perfluoroalkyl substances in the Laurentian Great Lakes. Environmental Science: Processes & Impacts 2019.

Saad, A.; Mills, R.; Wan, H.; Mottaleb, M. A.; Ormsbee, L.; Bhattacharyya, D., Thermo-responsive adsorption-desorption of perfluoroorganics from water using PNIPAm hydrogels and pore functionalized membranes. Journal of Membrane Science 2020, 599, 117821.

Scalfani, V. F.; Al Alshaikh, A.; Bara, J. E., Analysis of the Frequency and Diversity of 1,3-Dialkylimidazolium Ionic Liquids Appearing in the Literature. Industrial & Engineering Chemistry Research 2018, 57 (47), 15971-15981.

Senevirathna, S.; Tanaka, S.; Fujii, S.; Kunacheva, C.; Harada, H.; Shivakoti, B. R.; Okamoto, R., A comparative study of adsorption of perfluorooctane sulfonate (PFOS) onto granular activated carbon, ion-exchange polymers and non-ion-exchange polymers. Chemosphere 2010, 80 (6), 647-651.

Shannon MS, Bara JE. Properties of alkylimidazoles as solvents for CO2 capture and comparisons to imidazolium-based ionic liquids. Industrial & Engineering Chemistry Research. Jul. 20, 2011;50(14):8665-77.

Shannon, M. S.; Hindman, M. S.; Danielsen, S. P. O.; Tedstone, J. M.; Gilmore, R. D.; Bara, J. E., Properties of alkylbenzimidazoles for CO2 and SO2 capture and comparisons to ionic liquids. Science China Chemistry 2012, 55 (8), 1638-1647.

Shannon, M. S.; Irvin, A. C.; Liu, H.; Moon, J. D.; Hindman, M. S.; Turner, C. H.; Bara, J. E., Chemical and Physical Absorption of SO2 by N-Functionalized Imidazoles: Experimental Results and Molecular-level Insight. Industrial & Engineering Chemistry Research 2015, 54 (1), 462-471.

Shannon, M. S.; Tedstone, J. M.; Danielsen, S. P. O.; Bara, J. E., Evaluation of Alkylimidazoles as Physical Solvents for CO2/CH4 Separation. Industrial & Engineering Chemistry Research 2012, 51 (1), 515-522.

Shannon, M. S.; Tedstone, J. M.; Danielsen, S. P. O.; Hindman, M. S.; Irvin, A. C.; Bara, J. E., Free Volume as the Basis of Gas Solubility and Selectivity in Imidazolium-Based Ionic Liquids. Industrial & Engineering Chemistry Research 2012, 51 (15), 5565-5576.

Suresh, P.; Duval, C. E., Poly(acid)-Functionalized Membranes to Sequester Uranium from Seawater. Industrial & Engineering Chemistry Research 2020, 59 (26), 12212-12222.

Szala-Bilnik, J.; Abedini, A.; Crabtree, E.; Bara, J. E.; Turner, C. H., Molecular Transport Behavior of CO2 in Ionic Polyimides and Ionic Liquid Composite Membrane Materials. The Journal of Physical Chemistry B 2019, 123 (34), 7455-7463.

Szala-Bilnik, J.; Crabtree, E.; Abedini, A.; Bara, J. E.; Turner, C. H., Solubility and diffusivity of CO2 in ionic polyimides with [C(CN)3]x[oAc]1-x anion composition. Computational Materials Science 2020, 174, 109468.

Trnovec, H.; Doles, T.; Hribar, G.; Furlan, N.; Podgornik, A., Characterization of membrane adsorbers used for impurity removal during the continuous purification of monoclonal antibodies. Journal of Chromatography A 2020, 1609, 460518.

Turner, C. H.; Cooper, A.; Zhang, Z.; Shannon, M. S.; Bara, J. E., Molecular Simulation of the Thermophysical Properties of N-Functionalized Alkylimidazoles. The Journal of Physical Chemistry B 2012, 116 (22), 6529-6535.

Verevkin SP, Zaitsau DH, Emel'yanenko VN, Paulechka YU, Blokhin AV, Bazyleva AB, Kabo GJ. Thermodynamics of ionic liquids precursors: 1-methylimidazole. The Journal of Physical Chemistry B. Apr. 21, 2011;115(15):4404-11.

Verevkin, S. P.; Zaitseva, K. V.; Stanton, A. D.; Hindman, M. S.; Irvin, A. C.; Bara, J. E., Building Blocks for Ionic Liquids: Vapor Pressures and Vaporization Enthalpies of N-Functionalized Imidazoles with Branched and Cycloalkyl Substituents. Industrial & Engineering Chemistry Research 2015, 54 (40), 9850-9856.

Vivaldo-Lima, E.; Wood, P. E.; Hamielec, A. E.; Penlidis, A., An Updated Review on Suspension Polymerization. Industrial & Engineering Chemistry Research 1997, 36 (4), 939-965.

Vu, A.; Qian, X.; Wickramasinghe, S. R., Membrane-based hydrophobic interaction chromatography. Separation Science and Technology 2017, 52 (2), 287-298.

Wang, F.; Lu, X.; Shih, K. M.; Wang, P.; Li, X., Removal of perfluoroalkyl sulfonates (PFAS) from aqueous solution using permanently confined micelle arrays (PCMAs). Separation and Purification Technology 2014, 138, 7-12.

Wang, F.; Shih, K.; Leckie, J. O., Effect of humic acid on the sorption of perfluorooctane sulfonate (PFOS) and perfluorobutane sulfonate (PFBS) on boehmite. Chemosphere 2015, 118, 213-218.

Wang, S.; Yang, Q.; Chen, F.; Sun, J.; Luo, K.; Yao, F.; Wang, X.; Wang, D.; Li, X.; Zeng, G., Photocatalytic degradation of perfluorooctanoic acid and perfluorooctane sulfonate in water: A critical review. Chemical Engineering Journal 2017, 328, 927-942.

(56) References Cited

OTHER PUBLICATIONS

Wang, W.; Maimaiti, A.; Shi, H.; Wu, R.; Wang, R.; Li, Z.; Qi, D.; Yu, G.; Deng, S., Adsorption behavior and mechanism of emerging perfluoro-2-propoxypropanoic acid (GenX) on activated carbons and resins. Chemical Engineering Journal 2019, 364, 132-138.

Wang, Z.; MacLeod, M.; Cousins, I. T.; Scheringer, M.; Hungerbühler, K., Using COSMOtherm to predict physicochemical properties of poly- and perfluorinated alkyl substances (PFASs). Environmental Chemistry 2011, 8 (4), 389-398.

Whitley, J. W.; Jeffrey Horne, W.; Danielsen, S. P. O.; Shannon, M. S.; Marshall, J. E.; Hayward, S. H.; Gaddis, C. J.; Bara, J. E., Enhanced photopolymerization rate & conversion of 1-vinylimidazole in the presence of lithium bistriflimide. European Polymer Journal 2014, 60, 92-97.

Wickramasinghe, S. R.; Grzenia, D. L., Adsorptive membranes and resins for acetic acid removal from biomass hydrolysates. Desalination 2008, 234 (1), 144-151.

Wu, X.; Wu, Y.; Chen, L.; Yan, L.; Zhou, S.; Zhang, Q.; Li, C.; Yan, Y.; Li, H., Bioinspired synthesis of pDA@GO-based molecularly imprinted nanocomposite membranes assembled with dendrites-like Ag microspheres for high-selective adsorption and separation of ibuprofen. Journal of Membrane Science 2018, 553, 151-162.

Wyart, Y.; Georges, G.; Deumié, C.; Amra, C.; Moulin, P., Membrane characterization by microscopic methods: Multiscale structure. Journal of Membrane Science 2008, 315 (1), 82-92.

Xu, B.; Ahmed, M. B.; Zhou, J. L.; Altaee, A.; Wu, M.; Xu, G., Photocatalytic removal of perfluoroalkyl substances from water and wastewater: Mechanism, kinetics and controlling factors. Chemosphere 2017, 189, 717-729.

Yu, M.; Renner, J. N.; Duval, C. E., A Lysine-Modified Polyethersulfone (PES) Membrane for the Recovery of Lanthanides. Frontiers in Chemistry 2020, 8 (512).

Yue, S.; Roveda, J. D.; Mittenthal, M. S.; Shannon, M. S.; Bara, J. E., Experimental Densities and Calculated Fractional Free Volumes of Ionic Liquids with Tri- and Tetra-substituted Imidazolium Cations. Journal of Chemical & Engineering Data 2018, 63 (7), 2522-2532.

Zaggia, A.; Conte, L.; Falletti, L.; Fant, M.; Chiorboli, A., Use of strong anion exchange resins for the removal of perfluoroalkylated substances from contaminated drinking water in batch and continuous pilot plants. Water Research 2016, 91, 137-146.

Zhang, D. Q.; Zhang, W. L.; Liang, Y. N., Adsorption of perfluoroalkyl and polyfluoroalkyl substances (PFASs) from aqueous solution—A review. Science of the Total Environment 2019, 694, 133606.

Zhang, Q.; Deng, S.; Yu, G.; Huang, J., Removal of perfluorooctane sulfonate from aqueous solution by crosslinked chitosan beads: sorption kinetics and uptake mechanism. Bioresource Technology 2011, 102 (3), 2265-2271.

Zhang, X.; Fang, X.; Li, J.; Pan, S.; Sun, X.; Shen, J.; Han, W.; Wang, L.; Zhao, S., Developing new adsorptive membrane by modification of support layer with iron oxide microspheres for arsenic removal. Journal of Colloid and Interface Science 2018, 514, 760-768.

Zhi, Y.; Liu, J., Adsorption of perfluoroalkyl acids by carbonaceous adsorbents: Effect of carbon surface chemistry. Environmental Pollution 2015, 202, 168-176.

Zhu, S.; Hamielec, A., 4.32—Polymerization Kinetic Modeling and Macromolecular Reaction Engineering. In Polymer Science: A Comprehensive Reference, Matyjaszewski, K.; Moller, M., Eds. Elsevier: Amsterdam, 2012; pp. 779-831.

Ziel, R.; Haus, A.; Tulke, A., Quantification of the pore size distribution (porosity profiles) in microfiltration membranes by SEM, TEM and computer image analysis. Journal of Membrane Science 2008, 323 (2), 241-246.

\* cited by examiner

MATERIALS FOR REDUCING ACIDS FROM LIQUID PHASES

CROSS REFERENCE TO RELATED APPLICATIONS

This application claims the benefit of priority to U.S. Provisional Application No. 63/069,366, filed on Aug. 24, 2020, which is incorporated by reference herein in its entirety.

FIELD

The subject matter disclosed herein generally relates to imidazole-containing polymer membranes and resin beads/particles and methods of their preparation. Also, the subject matter described herein generally relates to methods of using the imidazole-containing polymer membranes and resin beads described herein to remove acids from liquid phases.

BACKGROUND

Growing concerns over of the presence of per- and polyfluoroalkyl substances (PFAS) and other toxic acids have prompted major efforts to reduce such substances from soil and water. PFAS are used in a variety of applications, including in food packaging and as stain- and water-repellents. PFAS pose a significant health risk as they are known to bioaccumulate in fish, mammals, and humans. PFAS are highly resistant to breakdown in the environment due to their carbon-fluorine bond, which is one of the shortest and strongest bonds known. The current technology used to reduce PFAS from water include ion-exchange resins, quaternized functional materials, membranes, and activated carbons. A number of diverse technologies, including solvents, sorbents, and other concepts are currently at various stages of evaluation as potential solutions that can contribute to meeting the challenge of improving the efficiency of PFAS reduction. Efficient reduction of PFAS from water is challenging because the current technologies are not tailorable for specific acids. Further, the current technologies have high energy costs and/or are single use applications. New tailorable acid-reducing materials are needed to achieve a long-term, recyclable, energy-efficient technology for PFAS reduction from water. The materials and methods disclosed herein address these and other needs.

SUMMARY

In accordance with the purposes of the disclosed materials, compounds, compositions, and methods, as embodied and broadly described herein, the disclosed subject matter, in one aspect, relates to compounds and compositions and methods for preparing and using such compounds and compositions. In a further aspect, the disclosed subject matter relates to polymers, resin beads, and membranes made therefrom that can be used for the reduction of toxic acids from water in industrial water treatment and chemical industries. More specifically, imidazole-containing polymer membranes and resin beads and methods of their preparation are described herein. Also, the subject matter described herein generally relates to methods of using the imidazole-containing polymer membranes and resin beads described herein to reduce acids from liquid phases.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF FIGURES

The accompanying Figures, which are incorporated in and constitute a part of this specification, illustrate several aspects described below.

DETAILED DESCRIPTION

Figure 1:
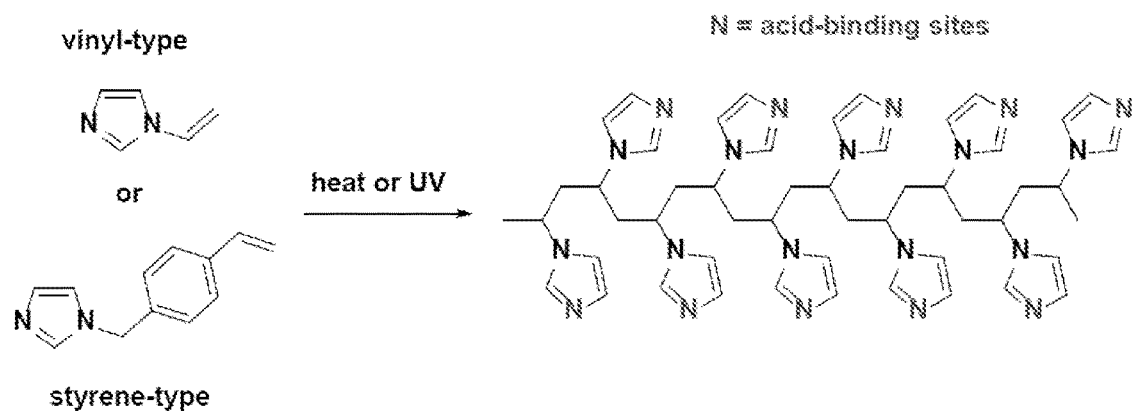
FIG. 1 is a general example of a poly(imidazole) polymer showing acid-binding sites.

The materials, compounds, compositions, articles, and methods described herein may be understood more readily by reference to the following detailed description of specific aspects of the disclosed subject matter and the Examples included therein.

Before the present materials, compounds, compositions, kits, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

By "reduce" or other forms of the word, such as "reducing" or "reduction," is meant lowering of an event or characteristic (e.g., PFAS in a stream). It is understood that this is typically in relation to some standard or expected value, in other words it is relative, but that it is not always necessary for the standard or relative value to be referred to. For example, "reduces PFAS" means reducing the amount of PFAS in a stream relative to a standard or a control. As used herein, reduce can include complete removal. In the disclosed method, reduction can refer to a 10%, 20%, 30%, 40%, 50%, 60%, 70%, 80%, 90%, or 100% decrease as compared to the standard or a control. It is understood that the term "reduce" includes adsorption and sequestration of an acid species onto the polymer. Further, it is understood that the terms "sequester," "adsorb," "capture," "remove," and "separate" can be used synonymously with the term "reduce."

By "treat" or other forms of the word, such as "treated" or "treatment," is meant to add or mix two or more compounds, compositions, or materials under appropriate conditions to produce a desired product or effect (e.g., to reduce or eliminate a particular characteristic or event such as PFAS). The terms "contact" and "react" are used synonymously with the term "treat."

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5 and are present in such ratio regardless of whether additional components are contained in the compound.

A weight percent (wt. %) of a component, unless specifically stated to the contrary, is based on the total weight of the formulation or composition in which the component is included.

The term "ion," as used herein, refers to any molecule, portion of a molecule, cluster of molecules, molecular complex, moiety, or atom that contains a charge (positive, negative, or both at the same time within one molecule, cluster of molecules, molecular complex, or moiety (e.g., Zwitterions)).

The term "anion" is a type of ion and is included within the meaning of the term "ion." An "anion" is any molecule, portion of a molecule (e.g., Zwitterion), cluster of molecules, molecular complex, moiety, or atom that contains a net negative charge.

The term "cation" is a type of ion and is included within the meaning of the term "ion." A "cation" is any molecule, portion of a molecule (e.g., Zwitterion), cluster of molecules, molecular complex, moiety, or atom, that contains a net positive charge.

The term "non-ionic" as used herein refers to being free of ionic groups or groups that are not readily substantially ionized in water. A "non-ionic" compound does not contain a charge at neutral pH (e.g., at a pH from 6.7 to 7.3). However, non-ionic compounds can be made to have a charge under acidic or basic conditions or by methods known in the art, e.g., protonation, deprotonation, oxidation, reduction, alkylation, acetylation, esterification, deesterification, hydrolysis, etc. Thus, the disclosed "non-ionic" compounds can become ionic under conditions where an acidic proton is available to protonate the compound.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. Unless specifically stated otherwise, a group that is said to be substituted can be substituted with alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent (s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted $C_3$-$C_8$ cycloalkyl moieties, the substituted moieties can, in addition, be specifically identified herein; for example, a particular substituted $C_3$-$C_8$ cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group with from 6 to 10 carbon atoms including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms, e.g., from 3 to 8 carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a shorthand notation for C=O.

The term "amino" as used herein is represented by the formula —NA$^1$A$^2$, where A$^1$ and A$^2$ can each be substitution group as described herein, such as hydrogen, alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" or "carboxyl" group as used herein is represented by the formula —C(O)O$^-$.

The term "ester" as used herein is represented by the formula —OC(O)A$^1$ or —C(O)OA$^1$, where A$^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula A$^1$OA$^2$, where A$^1$ and A$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula A$^1$C(O)A$^2$, where A$^1$ and A$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to a fluorine, chlorine, bromine, and iodine.

The term "hydroxyl" as used herein is represented by the formula —OH.

The term "nitro" as used herein is represented by the formula —NO$_2$.

The term "silyl" as used herein is represented by the formula —SiA$^1$A$^2$A$^3$, where A$^1$, A$^2$, and A$^3$ can be, independently, a hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2$A$^1$, where A$^1$ can be a hydrogen, alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "thiol" as used herein is represented by the formula —SH.

The term "thio" as used herein is represented by the formula —S—.

"R$^1$," "R$^2$," "R$^3$," "R$^n$," etc., where n is some integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

It is to be understood that the compounds provided herein may contain chiral centers. Such chiral centers may be of either the (R-) or (S-) configuration. The compounds provided herein may either be enantiomerically pure or be diastereomeric or enantiomeric mixtures.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples.

Materials and Compositions

Described herein are imidazole-containing polymers, resin beads, and membranes therefrom, as well as methods of using the polymers, resin beads, and membranes for the reduction of acids from liquid phases. Not to be bound by theory, it is likely that the strength of the interactions and rate of acid reduction are primarily influenced by the pK$_a$ of the imidazole group arising from type(s) and number of substituents attached to the imidazole core. Thus, the polymer physical properties (e.g., T$_g$), can be controlled via selected combinations of substituents attached to the imidazole core and the nature of the polymerizable group.

Imidazole Monomers Bearing Per- and Polyfluoroalkyl Groups

The polymer membranes and resin beads described herein are prepared from imidazole-based monomers with systematically varied 'X', 'Y', and/or 'Z' functionalities. These monomers can be used to fabricate thin films and resin beads of the homopolymer, copolymer, as well as blends with other polymers through techniques such as, for example, photopolymerization and heat. Imidazole-based materials offer the potential to achieve highly energy efficient acid reduction using polymer membranes and resin beads. The structure of the imidazole moiety can be tailored to change functional groups as a means of controlling pKa of the acid-binding site, which will govern the strength of the acid-base reaction between the polymer and PFAS.

Imidazoles can be used as starting materials for ionic liquids (ILs) and poly(ILs), which have shown promise as next-generation membrane materials for acid reduction due to their tunable structures, which controls membrane properties/performance. Like ILs, and all other modifiable cores, imidazoles offer the same advantages with respect to structure-performance tuning, but with the distinguishing feature of a Brønsted basic "pyridine-like" nitrogen (opposite the functionalized or "pyrrole-like" nitrogen), which can act as a H$^+$ acceptor or nucleophile. By tailoring the structure of the imidazole moiety, the energy costs for PFAS reduction can be minimized through regenerating the technology using a simple basic water solution.

The imidazole monomers bearing per- and polyfluoroalkyl groups described herein are represented by Formula I:

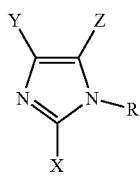
(I)

and derivatives thereof.

In Formula I, R is a polymerizable group. As used herein, a "polymerizable group" refers to portions of polymerizable compounds that are able to propagate free-radical polymerization, such as carbon-carbon double bonds. Examples of suitable R groups include vinyl-containing groups, acrylate-containing groups, and methacrylate-containing groups. In some examples, R includes substituted or unsubstituted styrene. Optionally, the substituted styrene can be α-methylstyrene. Further examples of polymerizable groups can be those groups that are able to propagate via condensation polymerization, such as amines and alcohols with isocyanates, or alcohols with esters or lactones.

Also in Formula I, X is $CF_3$ or $(CF_2)_nCF_3$, n is an integer 1 to 10.

Also in Formula I, Y and Z are each independently selected from hydrogen, halogen, hydroxyl, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted $C_3$-$C_8$ cycloalkyl, substituted or unsubstituted $C_2$-$C_8$ heterocycloalkyl, substituted or unsubstituted $C_6$-$C_{10}$ aryl, substituted or unsubstituted heteroaryl, substituted or unsubstituted thio, substituted or unsubstituted alkoxyl, substituted or unsubstituted $C_6$-$C_{10}$ aryloxyl, substituted or unsubstituted amino, cyano, or nitro. In certain examples, Y and Z are not all hydrogen.

In some examples, Y and Z can be electron withdrawing groups or electron donating groups. Examples of electron withdrawing groups include halogens (e.g., Cl), nitro, and cyano groups. Examples of electron donating groups include alkyl groups (e.g., methyl, ethyl, isopropyl) and amino groups.

Further in Formula I, Y and Z can be combined to form a substituted or unsubstituted $C_6$-$C_{10}$ aryl, substituted or unsubstituted heteroaryl, substituted or unsubstituted $C_3$-$C_8$ cycloalkyl, substituted or unsubstituted cycloalkenyl, substituted or unsubstituted cycloalkynyl, substituted or unsubstituted $C_2$-$C_8$ heterocycloalkyl, substituted or unsubstituted heterocycloalkenyl, or substituted or unsubstituted heterocycloalkynyl.

In some examples, the polymerizable group (i.e., R) of the imidazole monomers represented by Formula I can be selected from styrene, vinyl, or acrylate. In some examples of Formula I, R can be styrene as represented by Formula I-A. In other examples of Formula I, R can be vinyl as represented by Formula I-B. In still further examples of Formula I, R can be an acrylate group as represented by Formula I-C. In still further examples of Formula I, R can be a methacrylate group as represented by Formula 1-D. In still further examples of Formula I, R can be an acrylonitrile group as represented by Formula 1-E. In still other example of Formula I, R can be an alpha-methylvinyl as in Formula I-F. In still other example of Formula I, R can be an acrylamide as in Formula I-G.

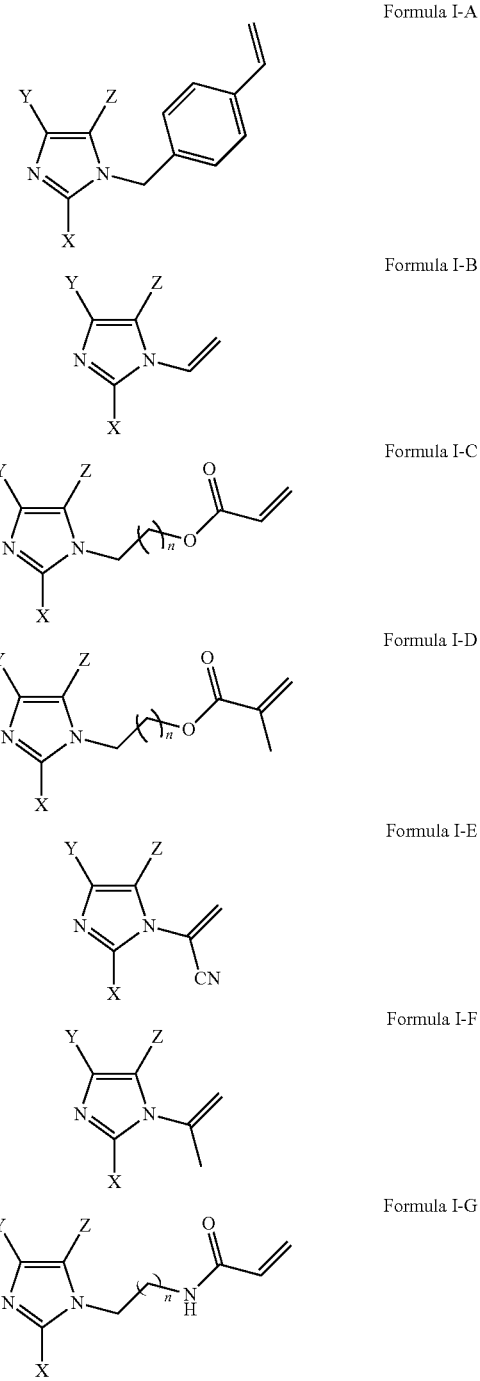

In Formula I-C, I-D and I-G, n is an integer from 0 to 10. In some examples, Y and Z in Formula I-A through I-G are each hydrogen.

In some examples, the imidazole substituents Y and Z can be each independently electron donating groups. In some examples, the imidazole substituents Y and Z can be each independently electron withdrawing groups.

In some examples, the imidazole substituents Y and Z can combine to form a substituted or unsubstituted $C_6$-$C_{10}$ aryl resulting in a benzimidazole group. The benzimidazole can be represented by Formula I-H.

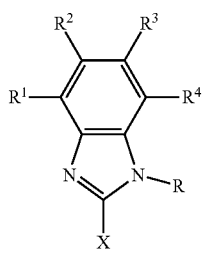

Formula I-H

In Formula I-H, $R^1$, $R^2$, $R^3$, and $R^4$ are each independently selected from hydrogen, halogen, hydroxyl, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted $C_3$-$C_8$ cycloalkyl, substituted or unsubstituted $C_2$-$C_8$ heterocycloalkyl, substituted or unsubstituted $C_6$-$C_{10}$ aryl, substituted or unsubstituted heteroaryl, substituted or unsubstituted thio, substituted or unsubstituted alkoxyl, substituted or unsubstituted $C_6$-$C_{10}$ aryloxyl, substituted or unsubstituted amino, cyano, or nitro.

Optionally, $R^1$, $R^2$, $R^3$, and $R^4$ in Formula I-H are each independently selected from an electron donating group or an electron withdrawing group.

Other Imidazole Monomers

The imidazole monomers herein can also be represented by Formula II:

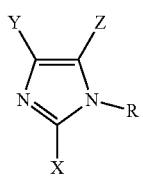

(II)

and derivatives thereof.

In Formula II, R is a polymerizable group. As used herein, a "polymerizable group" refers to portions of polymerizable compounds that are able to propagate via free-radical polymerization, such as carbon-carbon double bonds. Examples of suitable R groups include vinyl-containing groups, acrylate-containing groups, and methacrylate-containing groups. In some examples, R includes substituted or unsubstituted styrene. Optionally, the substituted styrene can be α-methylstyrene. Further examples of polymerizable groups can be those groups that are able to propagate via condensation polymerization, such as amines and alcohols with isocyantes, or alcohols with esters or lactones.

Also in Formula II, X, Y, and Z are each independently selected from the group consisting of hydrogen, halogen, hydroxyl, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted $C_3$-$C_8$ cycloalkyl, substituted or unsubstituted $C_2$-$C_8$ heterocycloalkyl, substituted or unsubstituted $C_6$-$C_{10}$ aryl, substituted or unsubstituted heteroaryl, substituted or unsubstituted thio, substituted or unsubstituted alkoxyl, substituted or unsubstituted $C_6$-$C_{10}$ aryloxyl, substituted or unsubstituted amino, cyano, nitro, and $CO_2CH_3$. In certain examples, X, Y, and Z are not all hydrogen.

In some examples, X, Y, and/or Z can be electron withdrawing groups or electron donating groups. Examples of electron withdrawing groups include halo (e.g., F, Cl, Br), nitro, cyano, or $CO_2CH_3$ groups. Examples of electron donating groups include alkyl groups (e.g., $C_{1-6}$ alkyl groups, such as methyl, ethyl, propyl, isopropyl, butyl, pentyl or hexyl) and amino groups.

Further in Formula II, Y and Z can be combined to form a substituted or unsubstituted $C_6$-$C_{10}$ aryl, substituted or unsubstituted heteroaryl, substituted or unsubstituted $C_3$-$C_8$ cycloalkyl, substituted or unsubstituted cycloalkenyl, substituted or unsubstituted cycloalkynyl, substituted or unsubstituted $C_2$-$C_8$ heterocycloalkyl, substituted or unsubstituted heterocycloalkenyl, or substituted or unsubstituted heterocycloalkynyl.

In some examples, the polymerizable group (i.e., R) of the imidazole monomers represented by Formula II can be selected from styrene, vinyl, or methacrylate. In some examples of Formula II, R can be styrene as represented by Formula II-A. In other examples of Formula II, R can be vinyl as represented by Formula II-B. In still further examples of Formula II, R can be an acrylate group as represented by Formula II-C. In still further examples of Formula II, R can be a methacrylate group as represented by Formula II-D. In still further examples of Formula II, R can be an acrylonitrile group as represented by Formula II-E. In still other example of Formula II, R can be an alpha-methylvinyl as in Formula II-F. In still other example of Formula II, R can be an acrylamide as in Formula II-G.

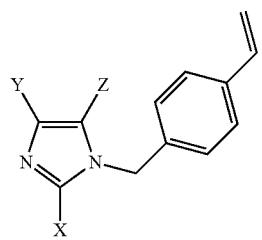

Formula II-A

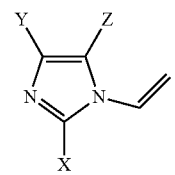

Formula II-B

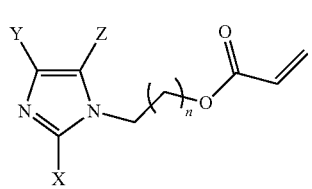

Formula II-C

-continued

Formula II-D
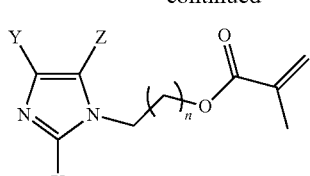

Formula II-E
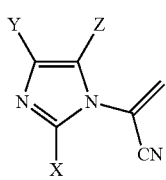

Formula II-F
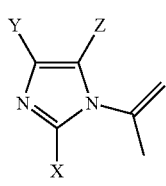

Formula II-G
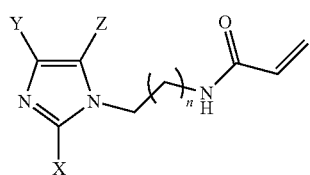

In Formula II-C, II-D, and II-G n is an integer from 0 to 10. In some examples, X, Y, and Z in Formula II-A through II-G are each hydrogen.

In some examples, the imidazole substituents X, Y, and/or Z can be electron donating groups. For example, the imidazole monomers can be represented by the following structures:

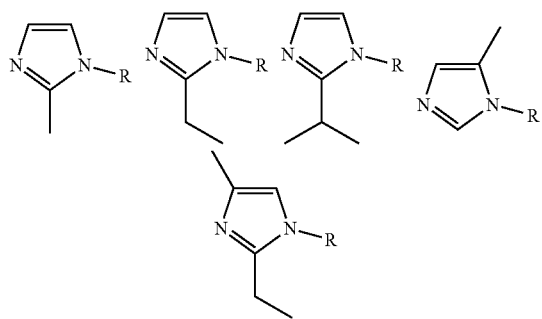

where R is a polymerizable group as defined herein, especially those shown in Formula II-A through II-G.

In some examples, the imidazole substituents X, Y, and/or Z can be electron withdrawing groups. For example, the imidazole monomers can be represented by the following structures:

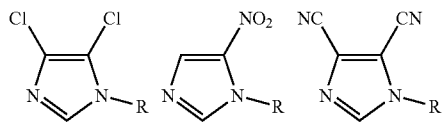

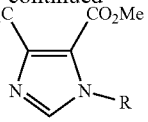

where R is a polymerizable group as defined herein, especially those shown in Formula II-A through II-G.

In a specific example, the compound is imidazole styrene Formula II-A were X, Y, and Z=H or 2-methylimidzole-styrene, Formula II-A where X=C=methyl, and Y and Z=H.

In some examples, the imidazole substituents Y and Z can combine to form a substituted or unsubstituted $C_6$-$C_{10}$ aryl resulting in a benzimidazole group. The benzimidazole can be represented by Formula II-H.

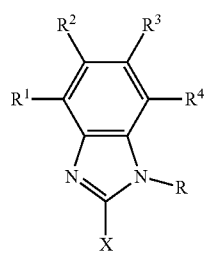

In Formula II-H, $R^1$, $R^2$, $R^3$, and $R^4$ can be independently selected from the group consisting of hydrogen, halogen, hydroxyl, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted $C_3$-$C_8$ cycloalkyl, substituted or unsubstituted $C_2$-$C_8$ heterocycloalkyl, substituted or unsubstituted $C_6$-$C_{10}$ aryl, substituted or unsubstituted heteroaryl, substituted or unsubstituted thio, substituted or unsubstituted alkoxyl, substituted or unsubstituted $C_6$-$C_{10}$ aryloxyl, substituted or unsubstituted amino, cyano, nitro, and $CO_2CH_3$.

Optionally, $R^1$, $R^2$, $R^3$, and $R^4$ in Formula II-H are independently selected from an electron donating group or an electron withdrawing group. For example, Formula II-H can be represented by the following structures:

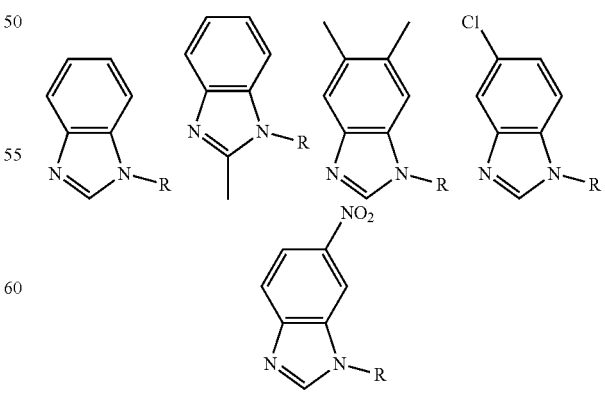

where R is a polymerizable group as defined herein, especially those shown in Formula II-A through II-H.

The imidazole monomers herein can also be represented by Formula III:

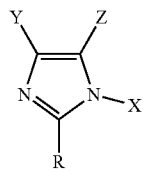
(III)

and derivatives thereof.

In Formula III, R is a polymerizable group. As used herein, a "polymerizable group" refers to portions of polymerizable compounds that are able to propagate via free-radical polymerization, such as carbon-carbon double bonds. Examples of suitable R groups include vinyl-containing groups, acrylate-containing groups, and methacrylate-containing groups. In some examples, R includes substituted or unsubstituted styrene. Optionally, the substituted styrene can be α-methylstyrene. Further examples of polymerizable groups can be those groups that are able to propagate via condensation polymerization, such as amines and alcohols with isocyantes, or alcohols with esters or lactones.

Also in Formula III, X, Y, and Z are each independently selected from the group consisting of hydrogen, halogen, hydroxyl, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted $C_3$-$C_8$ cycloalkyl, substituted or unsubstituted $C_2$-$C_8$ heterocycloalkyl, substituted or unsubstituted $C_6$-$C_{10}$ aryl, substituted or unsubstituted heteroaryl, substituted or unsubstituted thio, substituted or unsubstituted alkoxyl, substituted or unsubstituted $C_6$-$C_{10}$ aryloxyl, substituted or unsubstituted amino, cyano, nitro, and $CO_2CH_3$. In certain examples, X, Y, and Z are not all hydrogen.

In some examples, X, Y, and/or Z can be electron withdrawing groups or electron donating groups. Examples of electron withdrawing groups include halo (e.g., F, Cl, Br), nitro, cyano, or $CO_2CH_3$ groups. Examples of electron donating groups include alkyl groups (e.g., $C_{1-6}$ alkyl groups, such as methyl, ethyl, propyl, isopropyl, butyl, pentyl or hexyl) and amino groups.

Further in Formula III, Y and Z can be combined to form a substituted or unsubstituted $C_6$-$C_{10}$ aryl, substituted or unsubstituted heteroaryl, substituted or unsubstituted $C_3$-$C_8$ cycloalkyl, substituted or unsubstituted cycloalkenyl, substituted or unsubstituted cycloalkynyl, substituted or unsubstituted $C_2$-$C_8$ heterocycloalkyl, substituted or unsubstituted heterocycloalkenyl, or substituted or unsubstituted heterocycloalkynyl.

In some examples, the polymerizable group (i.e., R) of the imidazole monomers represented by Formula III can be selected from styrene, vinyl, or methacrylate. In some examples of Formula III, R can be styrene as represented by Formula III-A. In other examples of Formula III, R can be vinyl as represented by Formula III-B. In still further examples of Formula III, R can be an acrylate group as represented by Formula III-C. In still further examples of Formula III, R can be a methacrylate group as represented by Formula III-D. In still further examples of Formula II, R can be an acrylonitrile group as represented by Formula III-E. In still other example of Formula III, R can be an alpha-methylvinyl as in Formula III-F. In still other example of Formula III, R can be an acrylamide as in Formula III-G.

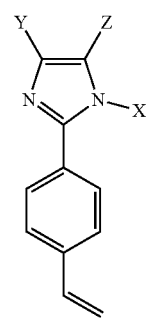
Formula III-A

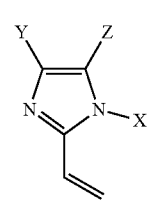
Formula III-B

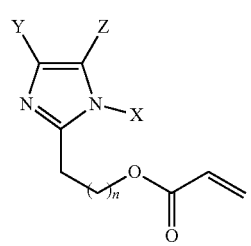
Formula III-C

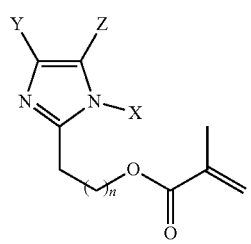
Formula III-D

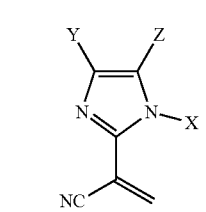
Formula III-E

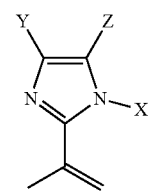
Formula III-F

Formula III-G

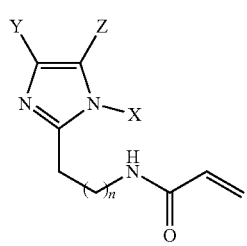

In Formula III-C, III-D, and III-G, n is an integer from 0 to 10. In some examples, X, Y, and Z in Formula III-A through III-G are each hydrogen.

In some examples, the imidazole substituents Y and Z can combine to form a substituted or unsubstituted $C_6$-$C_{10}$ aryl resulting in a benzimidazole group. The benzimidazole can be represented by Formula III-H.

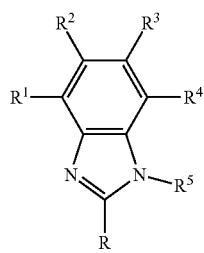

In Formula III-H, $R^1$, $R^2$, $R^3$, $R^4$ and $R^5$ can be independently selected from the group consisting of hydrogen, halogen, hydroxyl, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted $C_3$-$C_8$ cycloalkyl, substituted or unsubstituted $C_2$-$C_8$ heterocycloalkyl, substituted or unsubstituted $C_6$-$C_{10}$ aryl, substituted or unsubstituted heteroaryl, substituted or unsubstituted thio, substituted or unsubstituted alkoxyl, substituted or unsubstituted $C_6$-$C_{10}$ aryloxyl, substituted or unsubstituted amino, cyano, nitro, and $CO_2CH_3$; and R is a polymerizable group as disclosed herein.

Imidazole-Containing Polymers

One or more different types of the imidazole monomers described herein can be used to prepare the disclosed imidazole-containing polymers. In some examples, the imidazole-containing polymer is a homopolymer (e.g., the polymer is prepared by polymerizing a single selected monomer). In some examples, the imidazole-containing polymer is a co-polymer (e.g., the polymer is prepared by polymerizing two or more different monomers). Optionally, the two or more monomers used to prepare the co-polymer include at least one imidazole monomer as described herein. These can be polymerized with divinylbenzene, styrene, acrylate, methacrylate, methylmethacrylate, and the like. Optionally, the two or more monomers used to prepare the co-polymer include at least one imidazole monomer as described herein and at least one non-imidazole monomer. For example, the at least one non-imidazole monomer can be styrene, an acrylate monomer, a methacrylate monomer, a vinyl monomer, a poly(ethyleneglycol)-based monomer, or an ionic liquid-based monomer.

The disclosed polymers can comprise at least 10, 25, 50, 75, 100, or 200 repeating units. Further, the disclosed polymers can also be crosslinked for stability. Suitable crosslinkers can be di-vinyl compounds like divinylbenzene (e.g. at from 0.1 to 20 mol %).

Preparation of the Imidazole Monomers

The imidazole monomers according to Formula I, II, and III can be prepared in a variety of ways known to one skilled in the art of organic synthesis or variations thereon as appreciated by those skilled in the art. (References to a general formula like Formula I, is meant to also include related formula I-A through I-II, and the like.) The compounds described herein can be prepared from readily available starting materials. Optimum reaction conditions can vary with the particular reactants or solvents used, but such conditions can be determined by one skilled in the art. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

Variations on Formula I, II, and III include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups.

The imidazole monomers or the starting materials and reagents used in preparing the disclosed compounds are either available from commercial suppliers such as Aldrich Chemical Co., (Milwaukee, Wis.), Acros Organics (Morris Plains, N.J.), Fisher Scientific (Pittsburgh, Pa.), Sigma (St. Louis, Mo.), Pfizer (New York, N.Y.), GlaxoSmithKline (Raleigh, N.C.), Merck (Whitehouse Station, N.J.), Johnson & Johnson (New Brunswick, N.J.), Aventis (Bridgewater, N.J.), AstraZeneca (Wilmington, Del.), Novartis (Basel, Switzerland), Wyeth (Madison, N.J.), Bristol-Myers-Squibb (New York, N.Y.), Roche (Basel, Switzerland), Lilly (Indianapolis, Ind.), Abbott (Abbott Park, Ill.), Schering Plough (Kenilworth, N.J.), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), or mass spectrometry, or by chromatography such as high performance liquid chromatography (HPLC) or thin layer chromatography (TLC).

Scheme 1 shows the preparation of two imidazole monomers bearing perfluoroalkyl groups of Formula I.

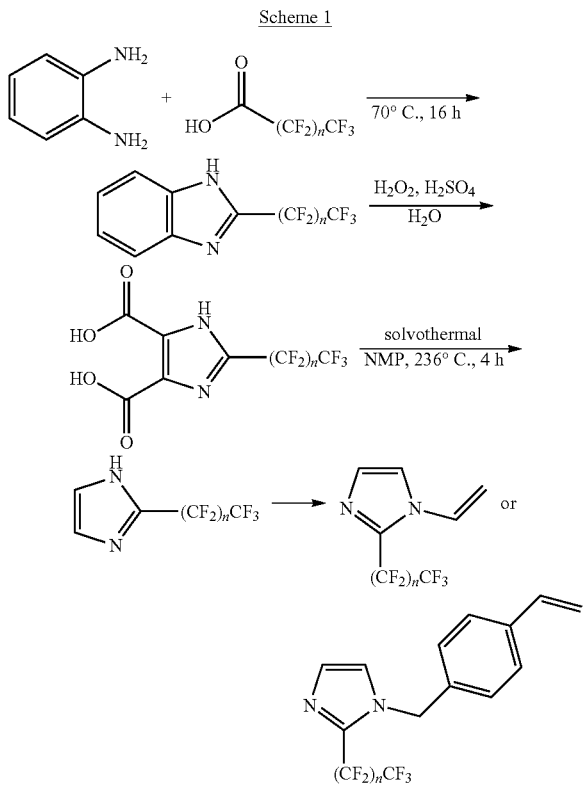

As shown in Scheme 2, the imidazole monomers of Formula II can be made, for example, by treating commercially available imidazole (1) with a base (e.g., sodium bicarbonate) to form the imidazolate sodium salt (2). The imidazolate sodium salt (2) can then be treated with a halide (e.g., vinylbenzylchloride) to form the N-substituted imidazole (3).

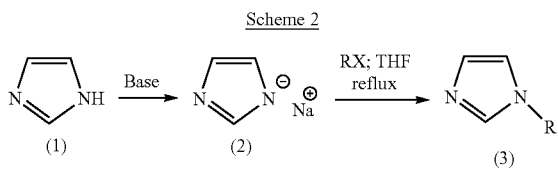

Preparation of the Imidazole-Containing Polymers

The imidazole-containing polymers can be prepared by polymerizing the imidazole monomers using, for example, photopolymerization or heat. The monomers can be photopolymerized neat or dissolved in a suitable solvent or mixture of solvents. In some examples, the photopolymerization process is substantially free of solvent. By "substantially free" is meant less than 5, 4, 3, 2, or 1 wt. % of the composition.

The monomers can be photopolymerized by irradiating the composition with UV-light (e.g., UVA at 320 to 390 nm or UVV at 395 to 445 nm), visible light, infrared radiation, X-rays, gamma rays, microwaves, or electron beam radiation. The radiation can be monochromatic or polychromatic, coherent or incoherent, and sufficiently intense to generate substantial numbers of free radicals in the photopolymerizable compositions. Suitable sources of such radiation include the sun, tungsten lamps, halogen lamps, fluorescent lamps, lasers, xenon lamps, carbon arcs, electron accelerators, cobalt 60, and mercury vapor discharge lamps.

Optionally, a photoinitiator can be used. Suitable examples of photoinitiators include benzophenones, acetophenone derivatives such as α-hydroxyalkylphenylketones, benzoin ethers, acylphosphonate derivatives, benzoin alkyl ethers and benzyl ketals, monoacylphosphine oxides, and bisacylphosphine oxides. Other examples of photoinitiators that can be used are ethyl 2,4,6-trimethylbenzoylphenyl phosphinate, 2 hydroxy-2-methyl-1-phenyl-propan-1-one, 2,2-dimethoxy-2phenylacetophenone, hydroxycyclohexylphenylketone, dimethoxylphenylacetophenone, mercaptobenzothiazoles, mercaptobenzooxazoles, hydroxy ketones, phenylglyoxylates, aminoketones, metallocenes, iodonium salts, and hexaryl bisimidazole, which are all commercially available or synthesizable by methods known in the art. Additional photoinitiators are disclosed in U.S. Pat. Nos. 5,472,992 and 5,218,009, which are incorporated by reference herein for their teachings of photoinitiators. In a preferred example, the photoinitiator is IRGACURE 1700™, DAROCUR 4265™, IRGACURE 819™, IRGACURE 819DW™, IRGACURE 2022™ or IRGACURE 2100™ or 2,2-dimethoxy-2-phenylacetophenone, which is commercially available from Ciba Additives (Basel, Switzerland). The photoinitiator can usually be used in an amount of less than about 10, 9, 8, 7, 6, 5, 4, 3, 2, or 1 wt. % of the monomers. However, higher amounts, such as greater than about 10 wt. % of photoinitiator can be used.

The monomer composition for photopolymerization can comprise additional components such as viscosity modifiers, surfactants, stabilizers, pigments, dyes, plasticizers, fillers, thermally stable inorganic materials, crosslinking agents, and the like. Suitable crosslinking agents can be found in U.S. Pat. No. 7,767,728, which is incorporated by reference herein for its teachings of crosslinking agents.

In one example, a reactive diluent can be present in the monomer compositions. A reactive diluent can be used to adjust the viscosity of the monomer composition and can be a low viscosity monomer capable of photopolymerization. Reactive diluents have a molecular weight of less than about 550 g/mol and can be used in the monomer composition in an amount of less than about 30, 25, 20, 15, 10, 5, or 1 wt. % of the monomer composition. Suitable reactive diluents can be found in U.S. Pat. Nos. 7,521,015 and 6,489,376, which are incorporated by reference herein for their teachings of reactive diluents.

Stabilizers can also be used. Examples of suitable stabilizers are non-acidic nitroso compounds, particularly N-nitrosohydroxylarylamines and derivatives thereof. Alternatively, the stabilizer can be an alkenyl substituted phenolic compound and one or more compounds chosen from a free radical scavenger, a hindered phenolic antioxidant, and a hydroxylamine derivative. Examples of suitable alkenyl substituted phenolic compounds include 2-propenylphenol, 4-acetoxy styrene, 2 allylphenol, isoeugenol, 2-ethoxy-5-propenylphenol, 2-allyl-4-methyl-6-t-butylphenol, 2-propenyl-4-methyl-6-t-butylphenol, 2-allyl-4,6-di-t-butylphenol, 2-propenyl-4,6-di-t-butylphenol, and 2,2'-diallyl-bisphenol A. A radical scavenger such as p-methoxy phenol (MEHQ) and a hindered phenolic antioxidant such as butylated hydroxy toluene (BHT) can be used as well.

The imidazole moiety of the imidazole-containing polymer is capable of reacting with and transporting acid species such as PFAS via solution-diffusion (i.e., non-reactive) or facilitated transport (i.e., reactive) mechanisms. Providing imidazole monomers used to prepare the imidazole-containing polymers depends, in one aspect, on the desired properties of the resulting polymer membrane and resin. The disclosed compositions can have multiple desired properties (e.g., low viscosity, low volatility, high $CO_2$ capacity, etc.), which, at least in part, come from the properties of the imidazoles used to prepare the polymer membranes and resins. Thus, to prepare the disclosed systems, one or more N-functionalized imidazoles with desired properties and, optionally, one or more additional monomers with desired properties are selected and provided. Properties desired to be adjusted based on the selection of the imidazole can include, for example, polymer physical properties (e.g., $T_g$), membrane transport properties (e.g., permeability of $CO_2$, $H_2O$, $N_2$, etc. and $CO_2$ selectivity), and chemical properties (e.g., $pK_a$ of imidazole group in polymer, hydrophilicity, swelling).

FIG. 1 shows a general depiction of the acid-binding sites of poly(imidazole) materials. As shown in FIG. 1, the poly(imidazoles) function as polymer Brønsted bases that will neutralize and bind strong protic acids such as PFAS. As the acid-base interactions are governed by $pK_a$, this platform can create chemical reactivity gradients within the membrane and resin and thus create a tunable, stable carrier for a number of species of interest. For example, polymer membranes and resins prepared from imidazoles substituted with electron donating groups can be used to prepare imidazoles with pKa values of about 7 to about 9.5. Depending on the target acid, the imidazole group can also be made less basic (i.e., to have a lower pKa) by using imidazoles substituted with electron withdrawing groups. Optionally, the polymer membranes and resins can include a combination of imidazoles substituted with electron withdrawing groups along with imidazoles substituted with electron donating groups to further tailor the membranes for each separation application. Optionally, the polymer membranes and resins can further include one or more metal cations. The metal cations can coordinate to the imidazoles as described herein within the polymer membrane and resin. Examples of suitable metal cations include $Zn^{2+}$ and $Ca^{2+}$.

Figure 2:
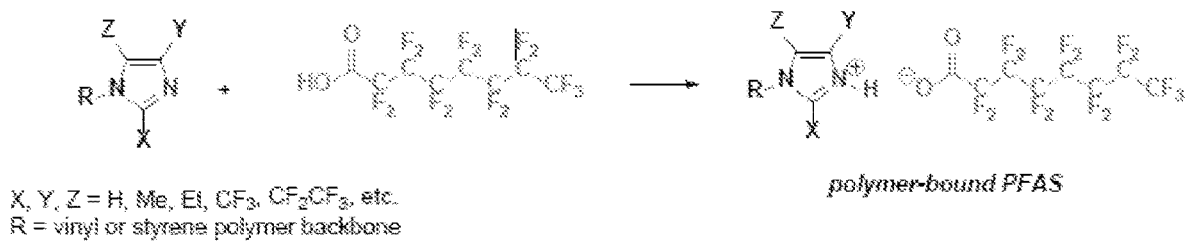
FIG. 2 is an example neutralization of perfluorooctanoic acid by poly(imidazole) to bind PFAS.

FIG. 2 shows an example neutralization of perfluorooctanoic acid (PFOA) by poly(imidazole) to bind PFAS. The structure of the imidazole moiety can be tailored to change functional groups as a means of controlling pKa of the acid-binding site, which will govern the strength of the acid-base reaction between the polymer and PFAS.

The functional groups appended to the imidazole ring can be selected to control the $pK_a$ of the acid-binding site which will govern the strength of the acid-base reaction between the polymer and PFAS acid. The $pK_a$ values of 2-fluoroalkylimidazoles will decrease to within the range of 5-6.5, but the poly(imidazoles) formed from monomers with fluoroalkyl substituents will still be sufficiently basic to deprotonate PFAS acid molecules, which are strong acids and have $pK_a$ values in the ranges of −3 (Perfluorooctanesulfonic Acid, PFOS), −0.3 (PFOA), and ~3 (Perfluorobutyl Sulfonamide, FBSA). Because $pK_a$ is a logarithmic measure, a difference of 3 $pK_a$ units between a base (B) and acid (HA) (e.g., 6−3=3) is considered to be quantitative (i.e., 99.9%) deprotonation, with the equilibrium fully favoring the products (i.e., B+HA→BH++A−). Furthermore, strategies that form copolymers from fluorinated imidazole monomers (e.g., 1-vinyl-2-trifluoromethylimidazole) with alkylimidazoles (e.g, 1-vinyl-2-methylimidazole) may provide the optimal combination of properties. The relatively wide range of $pK_a$ values for both imidazole and PFAS species also presents the opportunity for the selective separation of PFAS from each other. For example, a mixture of PFOA and FBSA in contact with a weakly basic poly(imidazole) with multiple electron-withdrawing groups on the imidazole ring resulting in a $pK_a$ of 3. This poly(imidazole) would still strongly bind PFOA, but not FBSA based on $pK_a$ differences. Thus, PFOA could be separated from FBSA by this poly(imidazole). Then, a second poly(imidazole) resin with electron-donating groups with a pKa of 7+ could bind the PFOA. In this way, a series of poly(imidazole) resins can not only remove PFAS acids but separate PFAS acids from each other. Such tunability could allow for better diagnostics of contaminant species as well as potential recovery of PFAS acids for reprocessing.

Methods of Using the Systems

The systems described herein can be used to reduce acids from liquid phases. In some examples, the liquid phases can be water streams. The method for reducing an acid from a stream can include feeding the stream through an imidazole-containing polymer membrane or resin as described herein. The acid streams can contain mineral acids, such as HCl, HF, HBr, HI, $HClO_4$, $H_2SO_4$, $HNO_3$, $H_3PO_4$, $H_3BO_3$, and any mixture thereof.

In some examples, the polymer membrane or resin is comprised primarily of imidazoles substituted with electron donating groups. In other examples, the polymer membrane or resin is composed primarily of imidazoles substituted with electron withdrawing groups.

In some examples the PFAS reduced can include Perfluorooctanoic Acid (PFOA), Perfluorooctanesulfonic Acid (PFOS), Perfluorobutyric acid (PFBA), Perfluoropentaoic acid (PFPeA), Perfluorobutanesulfonic acid (PFBS), Perfluorohexanoic acid (PFHxA), Hexafluoropropylene Oxide Dimer Acid (GenX), ADONA, F-53B, Perfluorobutyl Sulfonamide (FBSA), and Hydro-EVE acid.

Another method described herein is a method for reducing stomach acids (e.g. hydrochloric acid).

The examples below are intended to further illustrate certain aspects of the methods and compositions described herein and are not intended to limit the scope of the claims.

Additionally, in some examples the poly(imidazole) material can be regenerated by contact with a base (e.g., NaOH).

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1: Baseline Property Data for Imidazoles and Imidazole-Containing Polymers Despite their use in pharmaceutical and biological applications and the ubiquity of 1-methylimidazole as a precursor for imidazolium-based ILs, only a handful of physical property data exist for even the simplest N-functionalized imidazoles (see Shannon et al., *Industrial & Engineering Chemistry Research* 2011, 50(14): 8665-8677; Emel'yanenko et al., *Journal of Chemical Thermodynamics* 2011, 43(10): 1500-1505; Verevkin et al., *Journal of Physical Chemistry B* 2011, 115(15): 4404-4411). Furthermore, work to date has only focused on the liquid state of these materials. Other than for poly(vinylimidazole), which has been primarily examined for its chelation properties, little effort has been given to design imidazole-based monomers and tailored polymers (see Anderson et al., *Polymer* 2010, 51(12): 2447-2454; Green et al., *European Polymer Journal* 2011, 47(4): 486-496). N-vinylimidazole, while a polymerizable imidazole, only offers limited potential, as it has been reported to exhibit slow polymerization kinetics and does not offer a convenient means by which to control or systematically vary properties, such as $pK_a$.

Homopolymers of styrene-based derivatives (R=styrene) of imidazole (X, Y, Z=H), 2-methylimidazole (X=Me), 2-ethylimidazole (X=Et), 4-methylimidazole (Y=Me) and 2-ethyl-4-methylimidazole (X=Et, Y=Me) have been synthesized. With the $pK_a$ values of these imidazole structural groups (7-9.5), any polymer membrane or resin containing them is capable of facilitated transport of $CO_2$ as bicarbonate anion (FIG. 1), based on the $1^{st}$ $pK_a$ of $H_2CO_3$ (6.35). At room temperature, each of the homopolymers has been observed to be glassy rather than rubbery. Those materials containing imidazole with greater degrees of substitution were more flexible (i.e., less glassy) indicating that substitution not only has an effect on $pK_a$, but also on polymer physical properties. However, the materials transition to the rubbery state at 40-60° C. and/or upon exposure to moisture in the air. Furthermore, the imidazole-styrene monomers can be co-polymerized with PEG-acrylates, IL-based monomers, other imidazole-styrene monomers, and other monomers.

Example 2: Monomer Synthesis

An example synthetic method for an imidazole-based monomer is as follows: A 250 mL 2-necked round-bottomed flask equipped with a reflux condenser, volumetric addition funnel, and a magnetic stir bar was charged with a solution of sodium bicarbonate (5.25 g, 0.0625 mole) in a liquid mixture of 50 mL of water and 50 mL of acetone. Imidazole (13.6 g, 0.2 mole) was then added. Vinylbenzylchloride (7.6 g, 0.05 mole) was added drop-wise to the mixture over a period of about 10 minutes from the addition funnel. The flask was lowered into an oil bath thermostatted at 50° C., and the mixture was stirred for 20 hours.

The acetone was removed from the reaction mixture by rotary evaporation, and the residue was dissolved in 500 mL of diethyl ether. The solution was washed with 6×50 mL of deionized water, whereby the unreacted imidazole and any other water-soluble components were completely removed. Then, the product in the ether phase was back-extracted using 3×100 mL of a 2 M aqueous solution of hydrochloric acid. The solution was cooled in a refrigerator, and then 200 mL of a 4 N aqueous solution of sodium hydroxide was added to the hydrochloric acid solution. The deprotonated imidazole monomer product separated from the aqueous phase in the form of oil droplets. The product was separated via extraction with 3×50 mL of diethyl ether. A small amount of a quinone-based inhibitor was added, the ether phase was dried with anhydrous magnesium sulfate, and the solvent was removed via rotary evaporation. The product was further dried under dynamic vacuum (<1 torr). $^1$H NMR revealed an essentially pure imidazole monomer.

Example 3: Polymer Membrane Fabrication and Characterization

Thin films of homopolymers are produced via photopolymerization of imidazole-styrene monomers with increasing $pK_a$ based on imidazole, 2-methylimidazole, 2-ethylimidazole, 2-isopropylimidazole, 4-methylimidazole, and 2-ethyl-4-methylimidazole based on a technique as described in Bara et al., *Industrial & Engineering Chemistry Research* 2007, 46(16): 5397-5404; Bara et al., *Industrial & Engineering Chemistry Research* 2008, 47(24), 9919-9924; Bara et al., *Polymers for Advanced Technologies* 2008, 19 (10): 1415-1420; Bara et al., *Journal of Membrane Science* 2008, 321(1):3-7; Bara et al., *Journal of Membrane Science* 2008, 316(1-2):186-191; Bara et al., *Industrial & Engineering Chemistry Research* 2009, 48(9): 4607-4610; Bara et al., *Accounts of Chemical Research* 2010, 43(1): 152-159; and Bara et al., *Journal of Membrane Science* 2007, 288(1-2): 13-19.

An example membrane preparation is detailed herein. The monomer (~2 g) at 99 wt % is combined with a suitable photoinitiator (e.g., 2-hydroxy-2-methylpropiophenone) at 1 wt %. The solution is warmed and then homogenized using a vibrating stand mixer. Two identical, 6"×6" quartz plates of ¾" thickness are cleaned, and then coated with an agent that bonds to the quartz surface as a monolayer (e.g., Rain-X). This coating aids in the eventual release of the polymer from the plates. A highly porous polymer support (e.g., Pall Supor™ poly(ethersulfone)) is then cut to approximate dimensions of 60 cm×60 cm. The support is placed on the surface of one quartz plate, and the monomer-initiator mixture is then pipetted into the center of the support. The second quartz plate is then placed on top of the mixture and pressure is manually applied to distribute the monomer-initiator solution evenly and as thinly as possible. The plates are then placed in a reflective chamber and exposed to ultraviolet light with a wavelength of 254 nanometers. The polymerization reaction is allowed to proceed for ~3 hours. After this time, the ultraviolet light is switched off and the plates removed. A razor blade is inserted into the gap between the plates, and the top plate is liberated, leaving the supported polymer on the bottom plate. The razor is then used to carefully remove the polymer from the bottom plate, which is then transferred to a Teflon board. A steel cutting die of 47 mm diameter is then used to precisely cut the membrane from the bulk.

The remaining polymer is used for subsequent characterization via standard techniques including scanning electron microscopy (SEM) which is used to measure film thickness; differential scanning calorimetry (DSC), which is used to measure glass transition temperature; x-ray diffractometry (XRD) provides further information about polymer morphology; FT-IR which is used to calculate the degree of monomer conversion and estimate molecular weight; the goniometer is used to determine relative hydrophilicity/hydrophobicity via contact angle. The characterization data is utilized to correlate material performance with properties as well as suggest new polymers or co-polymers with tailored properties.

Example 4: Prepare Poly(Imidazole) Resin Beads Via Suspension Polymerization

The poly(imidazole) resin beads can be produced using a suspension polymerization of imidazole monomers. Suspension polymerization is a process in which monomer droplets are dispersed in water and each droplet acts as an individual microreactor, forming discrete polymer particles. Similar to other forms of polymerization, suspension polymerizations utilize an organic initiator (e.g., AIBN) and proceeds as a miniature bulk polymerization. As the polymerization reaction proceeds and monomers are transformed to polymer, the droplets increase in viscosity and as the polymerization completes, solid polymer particles are formed. In order to prevent droplets from sticking to each other and forming aggregate particles, high mixing rates and the addition of stabilizers in the aqueous phase (e.g., poly(vinylalcohol)) are also employed. Polymer particles in the range of 100s of micrometers to a few mm can be made in this manner. Suspension polymerization is particularly useful in the production of polymers from reactive monomers via radical polymerization. Water as the continuous phase facilitates agitation and promotes heat transfer. The viscosity of the suspension remains relatively constant with monomer conversion.

Generally, 25-50 g of an imidazole monomer are combined with ~1 wt % of a thermal initiator (e.g., AIBN) along with an optional crosslinker (e.g., divinylbenzene) at 1-5 wt %. The use of a crosslinker may help to limit any bead swelling when exposed to aqueous PFAS solutions. Optionally, 25-75 mL of a miscible, hydrophobic solvent (e.g., ethyl acetate) can also be added to this organic phase to create porosity in the beads via evaporation post-reaction. This organic phase is then dispersed in ~10× its volume (up to 500-1000 mL) of water in a 2 L insulated reactor and the two-phase mixture is stirred at a high shear rate while heated at 70-85° C. to initiate the polymerization and the reaction is run for ~6 h. After the polymerization is complete, the reaction is cooled, the beads are collected via vacuum filtration, washed with water, and dried under vacuum.

Example 5: Regenerating Poly(Imidazole) Adsorbents

Current adsorption techniques for PFAS do not regenerate under realistic adsorption conditions. The poly(imidazole) chemistry is capable of being regenerated by a simple basic solution because aqueous NaOH ($pK_a$=13.8) is a much stronger base than the imidazole groups used to bind PFAS. The poly(imidazole) adsorbents can be regenerated using aqueous solutions of various NaOH concentrations. The regeneration efficiency, calculated as the amount of PFAS released/the amount of PFAS adsorbed, can be determined as a function of time.

Example 6. Swelling Experiments

Imidazole0styrene (X=Y=Z=H) and 2-methylimidazolium (X=CH2, Y=Z=H) were tested in various acidic liquid media. The results are shown in Tables 1 and 2.

TABLE 1

| | Imidazole-Styrene Series: Before | | | | Imidazole-Styrene Series: After | | | | | | |
|---|---|---|---|---|---|---|---|---|---|---|---|
| ID | D* (mm) | T** (mm) | Vol (mm³) | Mass Before | D* (mm) | T** (mm) | Vol (mm³) | Vf/Vi (%) | Work Up | Mass After | |
| 53 | 10 | 1.10 | 86.39 | 0.1106 | 16.98 | 1.1 | 249.09 | 288 | Acid then Base | 0.16 | |
| 54 | 10 | 1.02 | 80.11 | 0.1104 | 18.20 | 1.23 | 319.99 | 399 | Acid then Water | 0.265 | |
| 55 | 10 | 0.82 | 64.40 | 0.0829 | 19.35 | 1.01 | 297.01 | 461 | Acid then Dry | 0.43 | |
| 56 | 11 | 0.72 | 68.42 | 0.0805 | 22.40 | 1.13 | 445.31 | 651 | Acid then Dry | 0.405 | HCl 100% |
| 57 | 11 | 0.79 | 75.08 | 0.0832 | 14.97 | 0.89 | 156.65 | 209 | Acid then Base | 0.1 | |
| 58 | 11 | 0.82 | 77.93 | 0.0893 | 26.33 | 1.69 | 920.19 | 1181 | Acid then Water | 0.42 | |
| 59 | 11 | 0.87 | 82.68 | 0.0711 | 18.47 | 0.75 | 200.95 | 243 | Acid then Dry | 0.115 | |
| 60 | 11 | 0.88 | 83.63 | 0.0688 | 18.49 | 1.12 | 300.73 | 360 | Acid then Dry | 0.135 | HCl 10% |
| 61 | 10 | 0.84 | 65.97 | 0.0806 | 14.69 | 0.95 | 161.01 | 244 | Acid then Base | 0.095 | |
| 62 | 10 | 0.46 | 36.13 | 0.0463 | 22.93 | 0.89 | 367.53 | 1017 | Acid then Water | 0.435 | |
| 63 | 10 | 0.85 | 66.76 | 0.0837 | 24.88 | 1.85 | 899.42 | 1347 | Acid then Dry | 0.525 | HCl 1% |
| 64 | 11 | 0.97 | 92.18 | 0.0872 | 25.33 | 1.45 | 730.68 | 793 | Acid then Dry | 0.66 | |
| 65 | 11 | 0.67 | 63.67 | 0.0647 | | | dissolved | | | | |
| 66 | 10 | 0.85 | 66.76 | 0.0785 | | | dissolved | | | | |
| 67 | 10 | 0.79 | 62.05 | 0.0726 | | | dissolved | | | | |
| 68 | 10 | 0.64 | 50.27 | 0.0605 | | | dissolved | | | | HOAc 100% |
| 69 | 11 | 0.65 | 61.77 | 0.0582 | 12.53 | 0.79 | 97.41 | 158 | Acid then Base | 0.085 | |
| 70 | 11 | 1.14 | 108.34 | 0.1036 | 19.45 | 1.56 | 463.50 | 428 | Acid then Water | 0.535 | |
| 71 | 11 | 0.98 | 93.13 | 0.0883 | 25.00 | 1.91 | 937.57 | 1007 | Acid then Dry | 0.985 | |
| 72 | 10 | 0.74 | 58.12 | 0.0660 | 25.00 | 1.27 | 623.41 | 1073 | Acid then Dry | 0.54 | HOAc 10% |
| 73 | 10 | 0.83 | 65.19 | 0.0870 | 13.60 | 0.96 | 139.46 | 214 | Acid then Base | 0.135 | |

TABLE 1-continued

| | Imidazole-Styrene Series: Before | | | | Imidazole-Styrene Series: After | | | | | | |
|---|---|---|---|---|---|---|---|---|---|---|---|
| ID | D* (mm) | T** (mm) | Vol (mm³) | Mass Before | D* (mm) | T** (mm) | Vol (mm³) | Vf/Vi (%) | Work Up | Mass After | |
| 74 | 11 | 1.00 | 95.03 | 0.1083 | 27.00 | 2.23 | 1276.80 | 1344 | Acid then Water | 0.95 | |
| 75 | 10 | 0.66 | 51.84 | 0.0665 | 25.00 | 0.98 | 481.06 | 928 | Acid then Dry | — | |
| 76 | 11 | 0.57 | 54.17 | 0.0659 | 27.00 | 1.24 | 709.97 | 1311 | Acid then Dry | 0.78 | HOAc 1% |
| 77 | 10 | 1.05 | 82.47 | 0.0850 | 9.86 | 0.72 | 54.98 | 67 | Acid then Base | 0.11 | |
| 78 | 10 | 1.18 | 92.68 | 0.0863 | 11.48 | 1.12 | 115.93 | 125 | Acid then Water | 0.085 | |
| 79 | 10 | 0.78 | 61.26 | 0.0747 | 25.00 | 2.35 | 1153.55 | 1883 | Acid then Dry | 0.375 | |
| 80 | 10 | 1.43 | 112.31 | 0.0978 | 25.00 | 2.78 | 1364.63 | 1215 | Acid then Dry | — | $HNO_3$ 100% |
| 81 | 10 | 1.23 | 96.60 | 0.0722 | 11.27 | 0.97 | 96.76 | 100 | Acid then Base | 0.085 | |
| 82 | 10 | 0.59 | 46.34 | 0.0560 | 20.15 | 0.86 | 274.24 | 592 | Acid then Water | 0.065 | $HNO_3$ 10% |
| 83 | 10 | 1.16 | 91.11 | 0.0726 | 12.44 | 0.93 | 113.04 | 124 | Acid then Dry | 0.12 | |
| 84 | 10 | 0.85 | 66.76 | 0.0762 | 12.45 | 0.75 | 91.30 | 137 | Acid then Dry | 0.105 | |
| 85 | 10 | 0.61 | 47.91 | 0.0572 | 14.23 | 0.65 | 103.37 | 216 | Acid then Base | 0.11 | |
| 86 | 10 | 0.99 | 77.75 | 0.0824 | 25.00 | 1.35 | 662.68 | 852 | Acid then Water | 0.595 | |
| 87 | 10 | 0.61 | 47.91 | 0.0534 | 19.22 | 0.85 | 246.61 | 515 | Acid then Dry | 0.06 | |
| 88 | 10 | 1.22 | 95.82 | 0.0844 | 16.74 | 1.68 | 369.75 | 386 | Acid then Dry | 0.105 | $HNO_3$ 1% |
| 89 | 10 | 0.82 | 64.40 | 0.0580 | 15.60 | 0.90 | 172.02 | 267 | Acid then Base | 0.21 | |
| 90 | 11 | 0.39 | 37.06 | 0.0754 | 18.04 | 0.82 | 209.59 | 566 | Acid then Water | 0.19 | |
| 91 | 10 | 1.41 | 110.74 | 0.0586 | 25.00 | 1.30 | 638.14 | 576 | Acid then Dry | — | |
| 92 | 10 | 1.59 | 124.88 | 0.0754 | 26.00 | 1.65 | 876.03 | 702 | Acid then Dry | — | $H_2SO_4$ 100% |
| 93 | 11 | 1.69 | 160.61 | 0.1606 | 12.84 | 4.10 | 530.89 | 331 | Acid then Base | 0.335 | |
| 94 | 11 | 1.81 | 172.01 | 0.1640 | 16.00 | 2.65 | 532.81 | 310 | Acid then Water | 0.235 | |
| 95 | 11 | 1.85 | 175.81 | 0.1895 | 17.27 | 2.67 | 625.44 | 356 | Acid then Dry | 0.615 | |
| 96 | 11 | 1.74 | 165.36 | 0.1471 | 16.61 | 2.07 | 448.54 | 271 | Acid then Dry | 0.485 | $H_2SO_4$ 10% |
| 97 | 11 | 2.35 | 223.33 | 0.1907 | 12.06 | 1.85 | 211.33 | 95 | Acid then Base | 0.2 | |
| 98 | 11 | 1.89 | 179.61 | 0.1643 | 17.97 | 1.94 | 492.03 | 274 | Acid then Water | 0.475 | |
| 99 | 11 | 2.37 | 225.23 | 0.2261 | 17.22 | 3.17 | 738.27 | 328 | Acid then Dry | 0.64 | $H_2SO_4$ 1% |
| 100 | 11 | 1.87 | 177.71 | 0.1654 | 14.72 | 1.97 | 335.25 | 189 | Acid then Dry | 0.185 | |
| 101 | 11 | 2.02 | 191.97 | 0.2013 | | | dissolved | | | | |
| 102 | 11 | 1.84 | 174.86 | 0.1594 | | | dissolved | | | | |
| 103 | 11 | 1.72 | 163.46 | 0.1567 | | | dissolved | | | | |
| 104 | 11 | 2.07 | 196.72 | 0.1624 | | | dissolved | | | | TFA 100% |
| 105 | 10 | 0.98 | 76.97 | 0.0760 | 11.94 | 1.1 | 123.17 | 160 | pure water | 0.09 | pure water |

D* = diameter; T** = thickness

TABLE 2

| | 2-Methyl-Imidazole-Styrene Series: Before | | | | 2-Methyl-Imidazole-Styrene Series: After | | | | | | |
|---|---|---|---|---|---|---|---|---|---|---|---|
| ID | D* (mm) | T** (mm) | Vol (mm³) | Mass Before | D* (mm) | T* (mm) | Vol (mm³) | Vf/Vi (%) | Work Up | Mass After | |
| 1 | 10 | 0.72 | 56.55 | 0.0449 | | | dissolved | | | | HCl |
| 2 | 10 | 1.19 | 93.46 | 0.1068 | | | dissolved | | | | 100% |
| 3 | 10 | 1.16 | 91.11 | 0.0967 | | | dissolved | | | | |
| 4 | 10 | 0.89 | 69.90 | 0.0633 | | | dissolved | | | | |
| 5 | 10 | 1.14 | 89.54 | 0.0806 | 10.49 | 1.10 | 95.07 | 106 | Acid then Base | 0.08 | HCl 10% |
| 6 | 10 | 0.66 | 51.84 | 0.0605 | 17.92 | 0.94 | 237.08 | 457 | Acid then Water | 0.065 | |
| 7 | 10 | 0.58 | 45.55 | 0.0461 | 15.71 | 0.57 | 110.49 | 243 | Acid then Dry | 0.06 | |
| 8 | 10 | 0.71 | 55.76 | 0.0561 | 15.58 | 0.79 | 150.61 | 270 | Acid then Dry | 0.075 | |
| 9 | 10 | 1.14 | 89.54 | 0.0770 | 13.20 | 1.12 | 153.27 | 171 | Acid then Base | 0.07 | HCl 1% |
| 10 | 10 | 0.77 | 60.48 | 0.0619 | 17.62 | 1.14 | 277.98 | 460 | Acid then Water | 0.06 | |
| 11 | 10 | 0.78 | 61.26 | 0.0568 | 16.26 | 1.06 | 220.11 | 359 | Acid then Dry | 0.06 | |
| 12 | 10 | 0.72 | 56.55 | 0.0508 | 15.20 | 0.93 | 168.76 | 298 | Acid then Dry | 0.05 | |
| 13 | 10 | 0.68 | 53.41 | 0.0464 | | | dissolved | | | | HOAc |
| 14 | 10 | 0.69 | 54.19 | 0.0482 | | | dissolved | | | | 100% |
| 15 | 10 | 0.75 | 58.90 | 0.0554 | | | dissolved | | | | |
| 16 | 10 | 0.59 | 46.34 | 0.0427 | | | dissolved | | | | |
| 17 | 10 | 1.17 | 91.89 | 0.0799 | | | dissolved | | | | HOAc |
| 18 | 10 | 0.88 | 69.11 | 0.0677 | | | dissolved | | | | 10% |
| 19 | 10 | 1.21 | 95.03 | 0.0929 | | | dissolved | | | | |
| 20 | 10 | 0.68 | 53.41 | 0.0454 | | | dissolved | | | | |
| 21 | 10 | 1.23 | 96.60 | 0.0912 | | | dissolved | | | | HOAc |
| 22 | 10 | 0.69 | 54.19 | 0.0406 | | | dissolved | | | | 1% |
| 23 | 10 | 0.64 | 50.27 | 0.0518 | | | dissolved | | | | |
| 24 | 10 | 0.76 | 59.69 | 0.0657 | | | dissolved | | | | |
| 25 | 10 | 0.66 | 51.84 | 0.0567 | | | dissolved | | | | $HNO_3$ |
| 26 | 10 | 0.81 | 63.62 | 0.0470 | | | dissolved | | | | 100% |
| 27 | 10 | 1.10 | 86.39 | 0.0788 | | | dissolved | | | | |
| 28 | 10 | 0.52 | 40.84 | 0.0372 | | | dissolved | | | | |
| 29 | 10 | 0.75 | 58.90 | 0.0489 | 11.61 | 0.69 | 73.05 | 124 | Acid then Base | 0.045 | $HNO_3$ 10% |
| 30 | 10 | 1.05 | 82.47 | 0.0617 | 22.16 | 0.89 | 343.26 | 416 | Acid then Water | 0.175 | |
| 31 | 10 | 0.76 | 59.69 | 0.0476 | 12.81 | 0.42 | 54.13 | 91 | Acid then Dry | 0.07 | |
| 32 | 10 | 0.84 | 65.97 | 0.0763 | 13.51 | 0.77 | 110.38 | 167 | Acid then Dry | 0.105 | |
| 33 | 10 | 0.94 | 73.83 | 0.0721 | 20.22 | 0.48 | 154.13 | 209 | Acid then Dry | 0.16 | $HNO_3$ 1% |
| 34 | 10 | 0.85 | 66.76 | 0.0605 | 19.39 | 1.23 | 363.20 | 544 | Acid then Dry | 0.145 | |
| 35 | 10 | 0.58 | 45.55 | 0.0437 | 17.4 | 0.48 | 114.14 | 251 | Acid then Base | | $H_2SO_4$ 100% |
| 36 | 10 | 0.72 | 56.55 | 0.0490 | 19 | 0.9 | 255.18 | 451 | Acid then Water | | |
| 37 | 10 | 1.06 | 83.25 | 0.0766 | 17.82 | 0.89 | 221.97 | 267 | Acid then Dry | 0.355 | |
| 38 | 10 | 0.84 | 65.97 | 0.0720 | 19.11 | 0.95 | 272.48 | 413 | Acid then Dry | 0.385 | |
| 39 | 10 | 0.50 | 39.27 | 0.0364 | 12.28 | 0.73 | 86.46 | 220 | Acid then Base | 0.05 | $H_2SO_4$ 10% |
| 40 | 10 | 0.73 | 57.33 | 0.0426 | 21.43 | 0.75 | 270.52 | 472 | Acid then Water | 0.04 | |
| 41 | 10 | 0.94 | 73.83 | 0.0676 | 19.12 | 1.1 | 315.83 | 428 | Acid then Dry | 0.365 | |
| 42 | 10 | 0.86 | 67.54 | 0.0650 | 19.61 | 0.92 | 277.86 | 411 | Acid then Dry | 0.29 | |
| 43 | 10 | 0.89 | 69.90 | 0.0552 | 13.95 | 1.12 | 171.18 | 245 | Acid then Base | 0.115 | $H_2SO_4$ 1% |
| 44 | 10 | 1.06 | 83.25 | 0.0813 | 16.33 | 1.12 | 234.57 | 282 | Acid then Water | 0.22 | |
| 45 | 10 | 0.66 | 51.84 | 0.0551 | 15.29 | 0.62 | 113.84 | 220 | Acid then Dry | 0.065 | |
| 46 | 10 | 1.17 | 91.89 | 0.1147 | 15.82 | 1.44 | 283.05 | 308 | Acid then Dry | 0.15 | |
| 47 | 10 | 1.17 | 91.89 | 0.0847 | | | dissolved | | | | TFA |
| 48 | 10 | 0.58 | 45.55 | 0.0477 | | | dissolved | | | | 100% |

TABLE 2-continued

| | 2-Methyl-Imidazole-Styrene Series: Before | | | | 2-Methyl-Imidazole-Styrene Series: After | | | | | | |
|---|---|---|---|---|---|---|---|---|---|---|---|
| ID | D* (mm) | T** (mm) | Vol (mm³) | Mass Before | D* (mm) | T* (mm) | Vol (mm³) | Vf/Vi (%) | Work Up | Mass After | |
| 49 | 10 | 1.22 | 95.82 | 0.1129 | | | dissolved | | | | |
| 50 | 10 | 1.26 | 98.96 | 0.1116 | | | dissolved | | | | |
| 51 | 10 | 0.71 | 55.76 | 0.0549 | 12.09 | 0.89 | 102.17 | 183 | Acid then Base | 0.055 | HNO₃ 1% |
| 52 | 10 | 0.47 | 36.91 | 0.0434 | 17.61 | 0.61 | 148.57 | 402 | Acid then Water | 0.05 | |
| 106 | 10 | 0.55 | 43.20 | 0.0457 | 11.71 | 0.56 | 60.31 | 140 | Pure Water | 0.05 | Pure Water |

D* = diameter; T** = thickness

These data show that HCl swelled the polymers (e.g., they would do well in stomach acid for example). The other acids, especially at higher concentrations, appeared to react (e.g., nitration) or simply dissolve/attack the styrene backbone. The addition of more functional groups at X, Y, Z can make them resistant to other acids while still swelling.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods and combinations of various features of the compounds and methods are intended to fall within the scope of the appended claims, even if not specifically recited. Thus, a combination of steps, elements, components, or constituents can be explicitly mentioned herein; however, all other combinations of steps, elements, components, and constituents are included, even though not explicitly stated.

What is claimed is:

1. A composition comprising an imidazole monomer bearing perfluoroalkyl groups having the following structure represented by Formula I:

and derivatives thereof, wherein:
  R is a polymerizable group;
  X is $CF_3$ or $(CF_2)_n CF_3$, n is an integer 1 to 10; and
  optionally one or more additional monomers.

2. The composition of claim 1, wherein R comprises a vinyl-containing group, an acrylate-containing group, or a methacrylate-containing group.

3. The composition of claim 1, wherein R is a vinyl group, acrylonitrile group, alpha-methylvinyl group, or an acrylamide group.

4. The composition of claim 1, wherein R is a substituted or unsubstituted styrene.

5. The composition of claim 4, wherein the substituted styrene is α-methylstyrene.

6. The composition of claim 1, where the one or more additional monomers are used and are selected from the group consisting of divinylbenzene, substituted or unsubstituted styrene, acrylate, methacrylate, and methylmethacrylate.

7. The composition of claim 6, wherein the substituted styrene is α-methylstyrene.

8. A method of preparing a polymer, comprising polymerizing a composition comprising the composition of claim 1.

* * * * *